(12) United States Patent
Parodi

(10) Patent No.: US 7,544,198 B2
(45) Date of Patent: *Jun. 9, 2009

(54) SYSTEMS AND METHODS FOR APPLYING A SUTURE WITHIN A BLOOD VESSEL LUMEN

(75) Inventor: Juan C Parodi, Buenos Aires (AR)

(73) Assignee: Aptus Endosystems, Inc., Sunnyvale, CA (US)

( * ) Notice: Subject to any disclaimer, the term of this patent is extended or adjusted under 35 U.S.C. 154(b) by 441 days.

This patent is subject to a terminal disclaimer.

(21) Appl. No.: 10/915,864

(22) Filed: Aug. 11, 2004

(65) Prior Publication Data

US 2005/0015100 A1   Jan. 20, 2005

Related U.S. Application Data

(62) Division of application No. 10/099,149, filed on Mar. 15, 2002, now Pat. No. 6,800,081, which is a division of application No. 09/787,135, filed on Jun. 4, 2001, now Pat. No. 6,592,593.

(60) Provisional application No. 60/101,050, filed on Sep. 18, 1998.

(30) Foreign Application Priority Data

Mar. 13, 1998   (AR) .............................. P980101145

(51) Int. Cl.
*A61B 17/10* (2006.01)
*A61B 19/00* (2006.01)

(52) U.S. Cl. ...................................... 606/139; 128/898

(58) Field of Classification Search ................. 606/139, 606/142, 198, 108, 107, 155; 623/1.11, 1.12, 623/1.23; 128/898
See application file for complete search history.

(56) References Cited

U.S. PATENT DOCUMENTS 2,033,039 A   3/1936   Limpert
3,686,740 A   8/1972   Shiley (Continued)

FOREIGN PATENT DOCUMENTS

EP   0321912 A1   12/1987

(Continued)

OTHER PUBLICATIONS

Advertising literature entitled "5mm Origin Tacker™ It Runs in Circles Around Staples"(origin) copyright 1995, with attached article entitled "The S piral Tacker: A New Technique for Stabilizing Prosthetic Mesh in Laparoscopic Hernia Repair" Nov. 1995, *Surgical Rounds*.

(Continued)

*Primary Examiner*—Pedro Philogene
(74) *Attorney, Agent, or Firm*—Ryan Kromholz & Manion S.C.

(57) ABSTRACT

Systems and methods apply a suture within a blood vessel lumen. The systems and methods advance within a blood vessel lumen a catheter tube having a distal region that carries a suture applicator. The systems and methods operate the suture applicator from a location external to the blood vessel lumen to apply a suture to an interior wall of a blood vessel lumen.

2 Claims, 30 Drawing Sheets

U.S. PATENT DOCUMENTS

| | | | |
|---|---|---|---|
| 3,799,172 A | 3/1974 | Szpur | |
| 4,140,126 A | 2/1979 | Choudhury | |
| 4,307,722 A | 12/1981 | Evans | |
| 4,580,568 A | 4/1986 | Gianturco | |
| 4,781,682 A | 11/1988 | Patel | |
| 4,898,577 A | 2/1990 | Badger et al. | |
| 4,921,484 A | 5/1990 | Hillstead | |
| 5,030,204 A | 7/1991 | Badger et al. | |
| 5,042,707 A | 8/1991 | Taheri | |
| 5,071,407 A | 12/1991 | Termin et al. | |
| 5,104,399 A | 4/1992 | Lazarus | |
| 5,304,184 A * | 4/1994 | Hathaway et al. | 606/144 |
| 5,330,490 A | 7/1994 | Wilk et al. | |
| 5,330,503 A | 7/1994 | Yoon | |
| 5,470,337 A | 11/1995 | Moss | |
| 5,480,382 A | 1/1996 | Hammerslag et al. | |
| 5,489,295 A | 2/1996 | Piplani et al. | |
| 5,562,728 A | 10/1996 | Lazarus et al. | |
| 5,571,171 A | 11/1996 | Barone et al. | |
| 5,571,173 A | 11/1996 | Parodi | |
| 5,582,616 A | 12/1996 | Bolduc et al. | |
| 5,639,278 A | 6/1997 | Dereume et al. | |
| 5,662,700 A | 9/1997 | Lazarus | |
| 5,676,696 A | 10/1997 | Marcade | |
| 5,676,697 A | 10/1997 | McDonald | |
| 5,700,269 A | 12/1997 | Pinchuk et al. | |
| 5,702,365 A | 12/1997 | King | |
| 5,713,907 A | 2/1998 | Hogendijk et al. | |
| 5,810,882 A * | 9/1998 | Bolduc et al. | 606/213 |
| 5,824,008 A | 10/1998 | Bolduc et al. | |
| 5,824,041 A | 10/1998 | Lenker et al. | |
| 5,855,565 A | 1/1999 | Bar-Cohen et al. | |
| 5,944,750 A | 8/1999 | Tanner et al. | |
| 5,957,940 A | 9/1999 | Tanner et al. | |
| 5,964,772 A | 10/1999 | Bolduc et al. | |
| 5,968,053 A | 10/1999 | Revelas | |
| 5,972,023 A | 10/1999 | Tanner et al. | |
| 5,980,548 A | 11/1999 | Evans et al. | |
| 5,993,401 A | 11/1999 | Inbe et al. | |
| 5,993,466 A | 11/1999 | Yoon | |
| 6,126,685 A | 10/2000 | Lenker et al. | |
| 6,145,509 A | 11/2000 | Tanner | |
| 6,217,597 B1 | 4/2001 | Tanner | |
| 6,248,118 B1 | 6/2001 | Tanner et al. | |
| 6,258,119 B1 * | 7/2001 | Hussein et al. | 623/1.22 |
| 6,270,516 B1 | 8/2001 | Tanner et al. | |
| 6,287,315 B1 | 9/2001 | Wijeratne et al. | |
| 6,296,656 B1 | 10/2001 | Bolduc et al. | |
| 6,302,906 B1 | 10/2001 | Goicoechea et al. | |
| 6,336,933 B1 * | 1/2002 | Parodi | 606/139 |
| 6,371,919 B1 | 4/2002 | Tanner et al. | |
| 6,409,757 B1 | 6/2002 | Trout, III et al. | |
| 6,428,565 B1 | 8/2002 | Wisselink | |
| 6,520,974 B2 | 2/2003 | Tanner et al. | |
| 6,544,253 B1 | 4/2003 | Tanner | |
| 6,562,051 B1 | 5/2003 | Bolduc et al. | |
| 6,592,593 B1 * | 7/2003 | Parodi et al. | 606/108 |
| 6,800,081 B2 * | 10/2004 | Parodi | 606/139 |

FOREIGN PATENT DOCUMENTS

| | | |
|---|---|---|
| EP | 0663184 A1 | 1/1994 |
| FR | 2 299 548 | 8/1976 |
| WO | WO 97/03616 | 2/1997 |
| WO | WO 99/53845 | 10/1999 |

OTHER PUBLICATIONS

MedPro Month Oct. 1995, "Laparoscopic Surgery".
Newman III, et al. Assisted TAPP Procedure Circa 1995.
Hatchet, Lawrence, et al. "Extraperitoneal Endoscopic Burch Repair Using a Tacker Mesh Technique", Circa 1995.

* cited by examiner

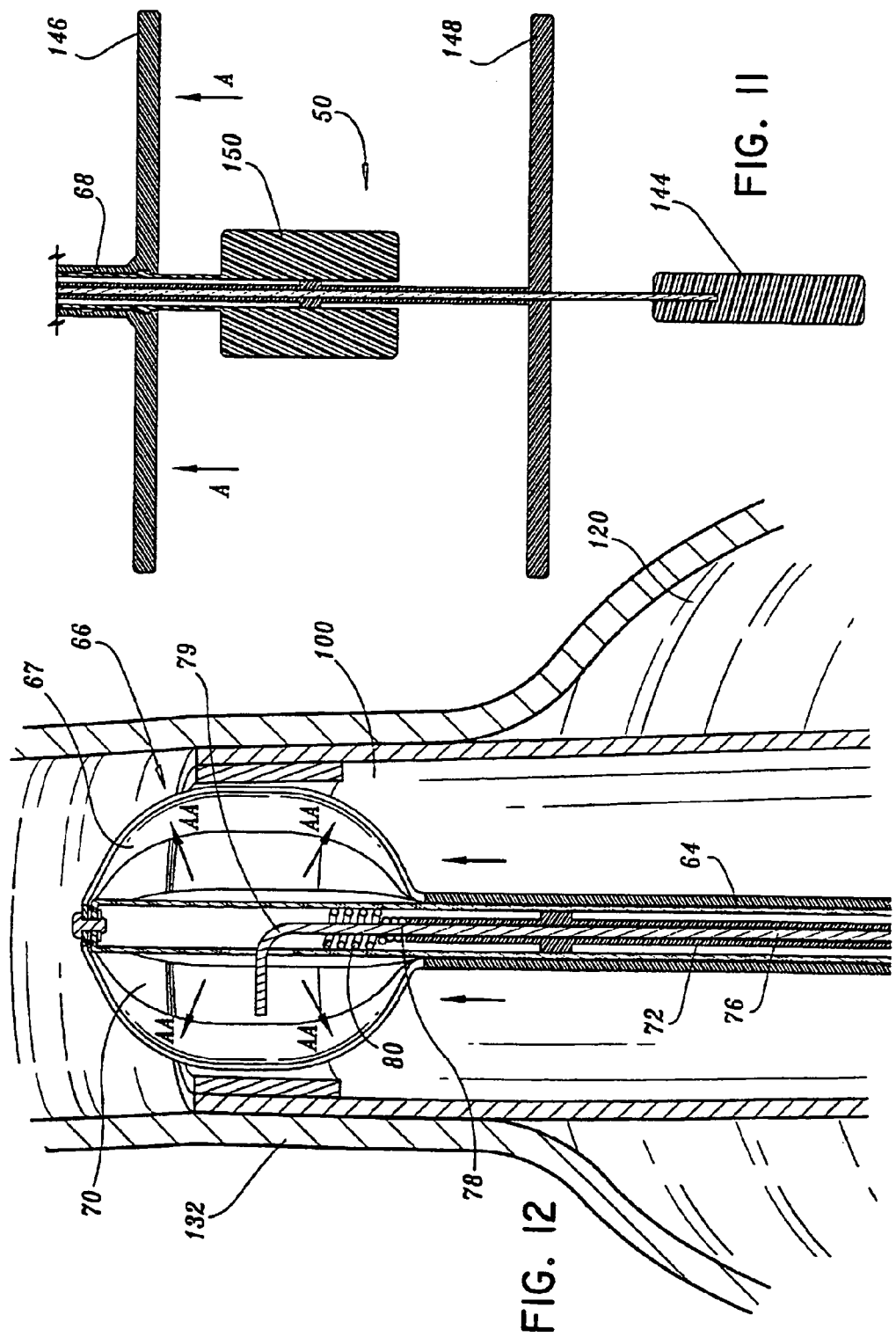

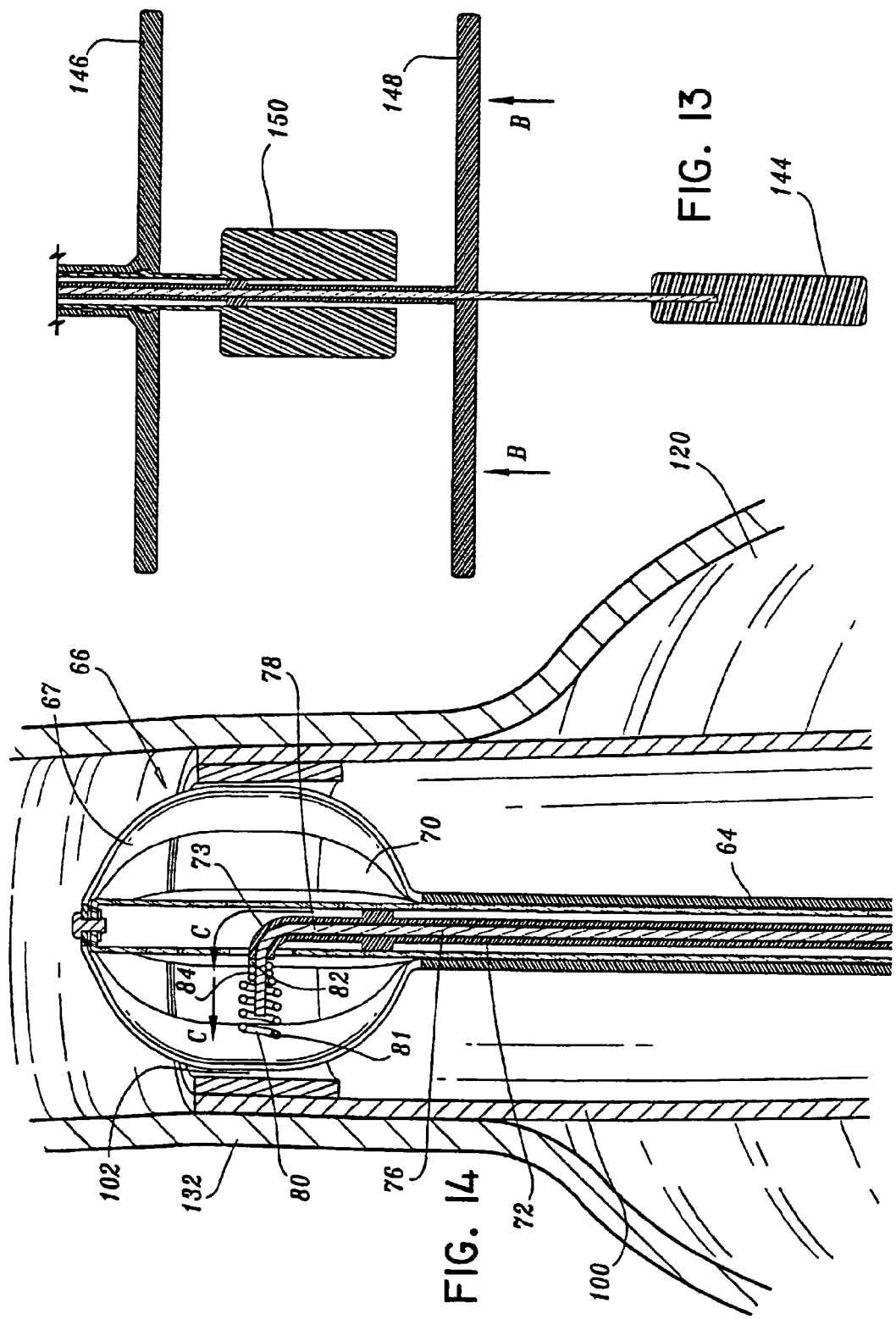

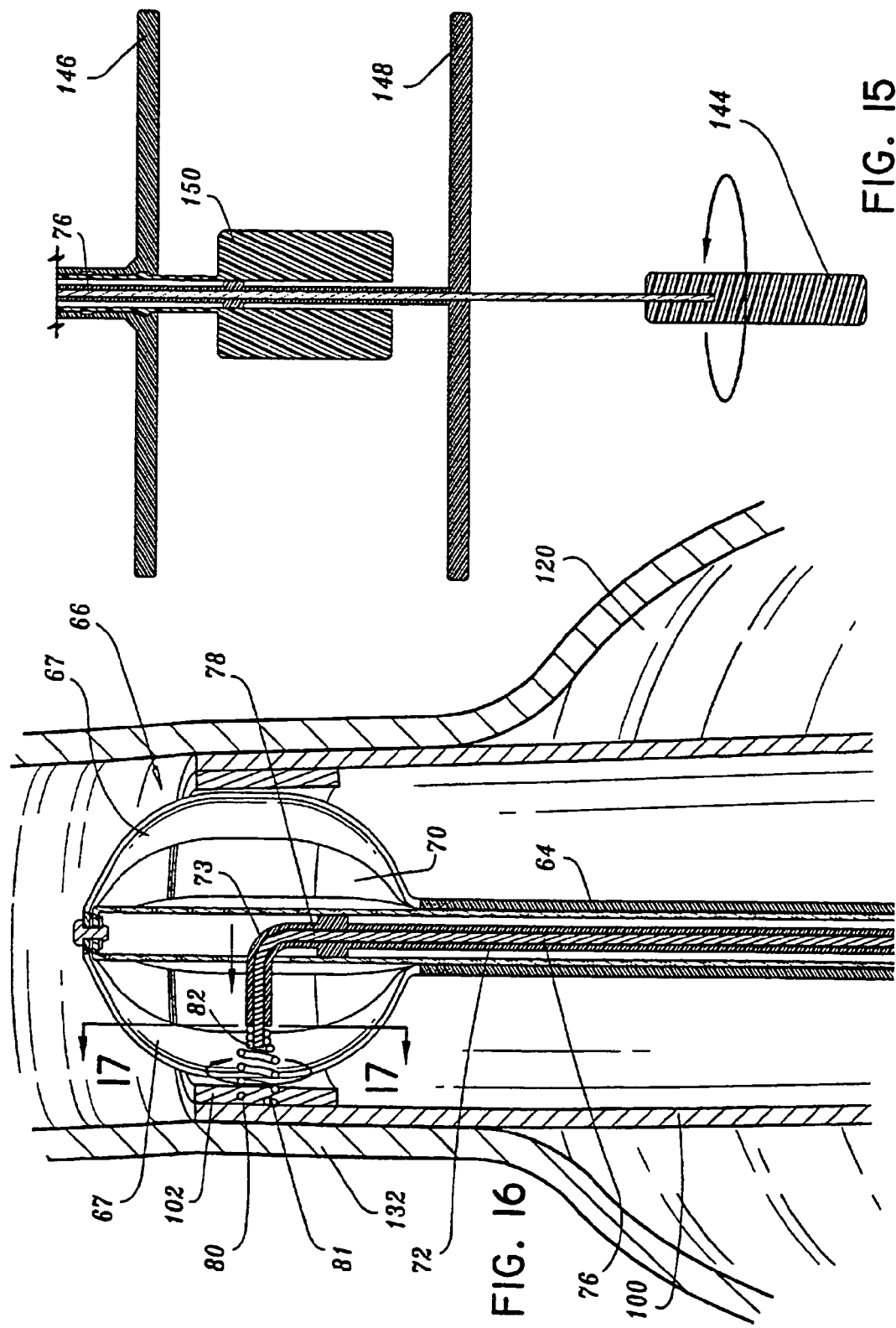

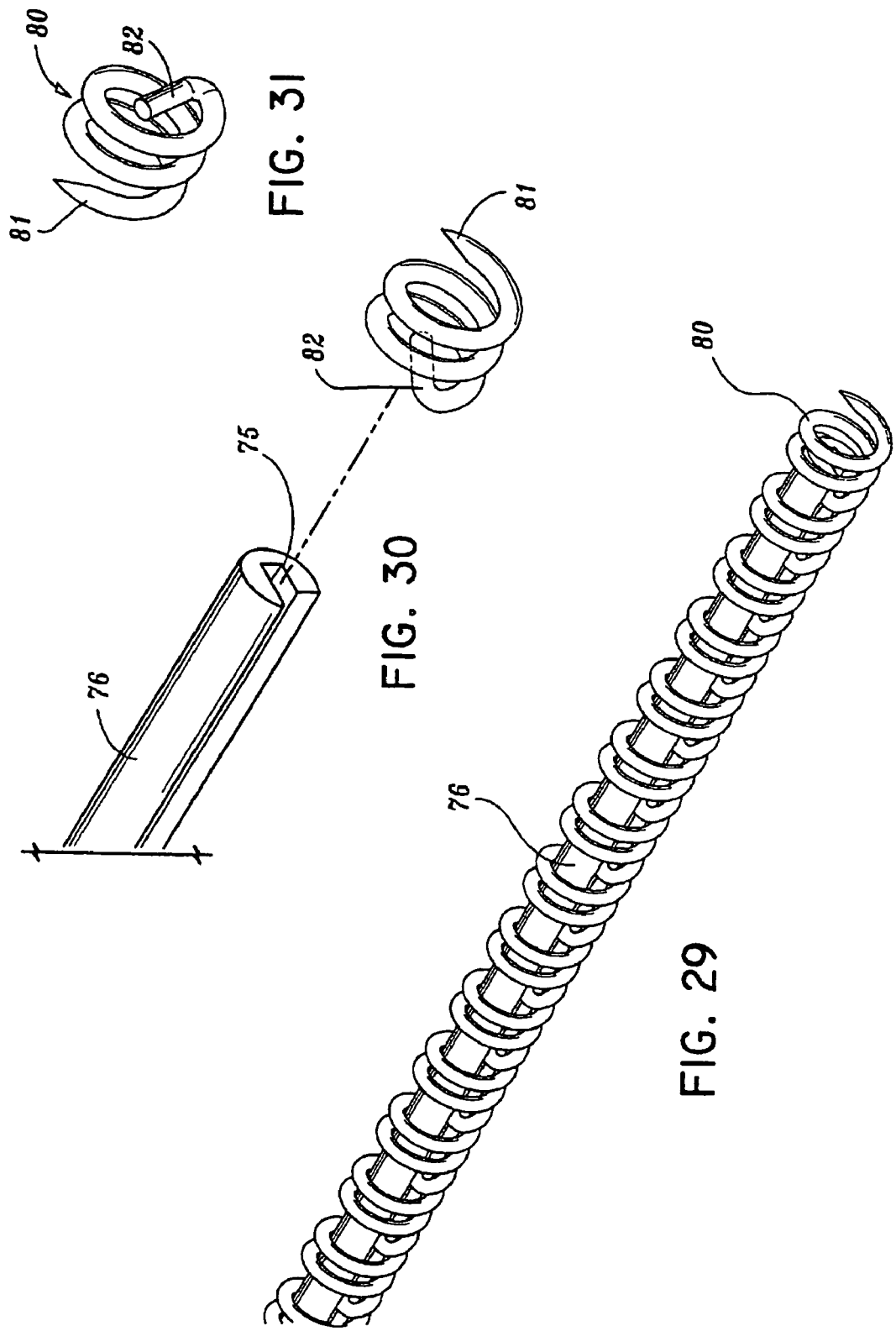

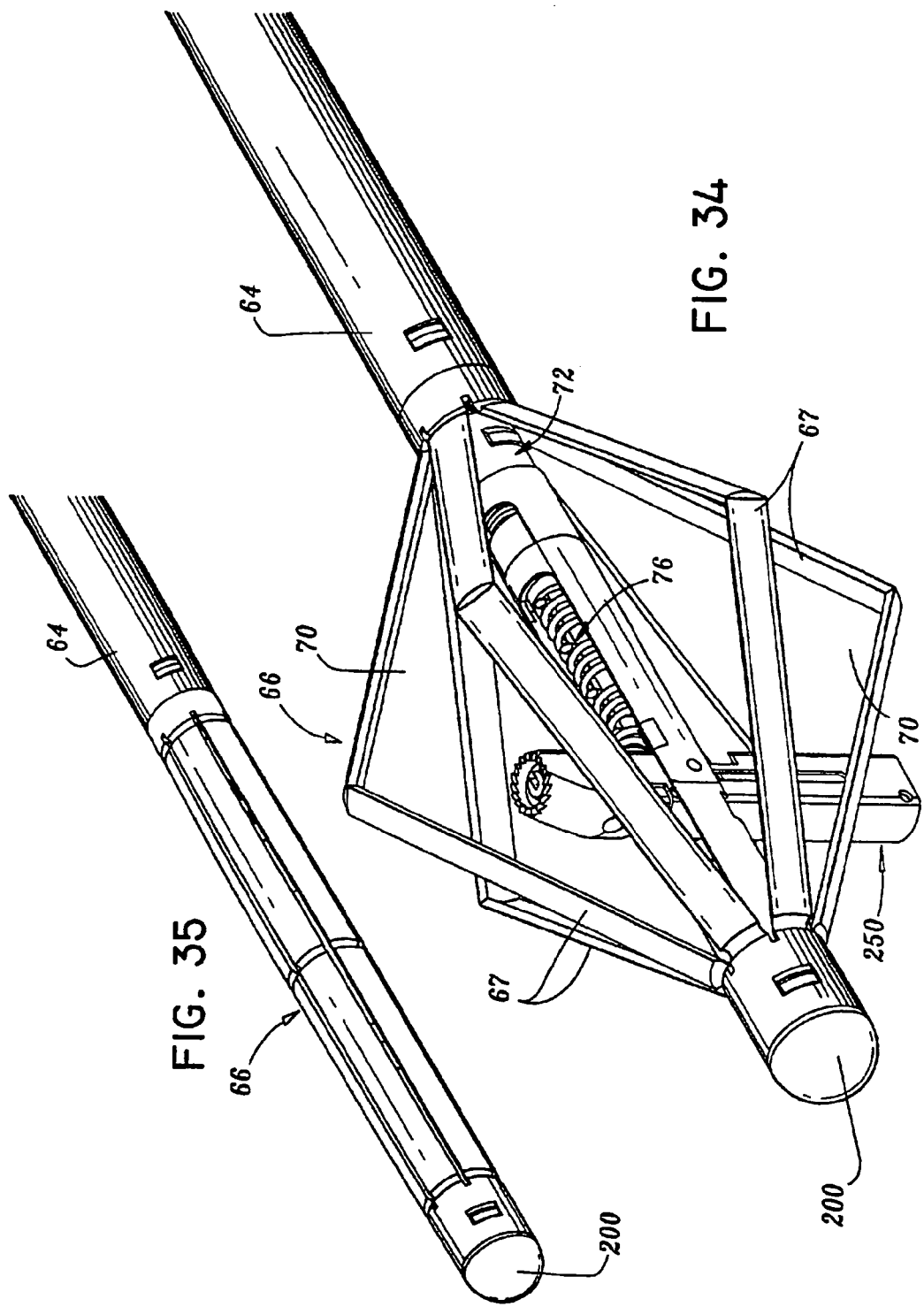

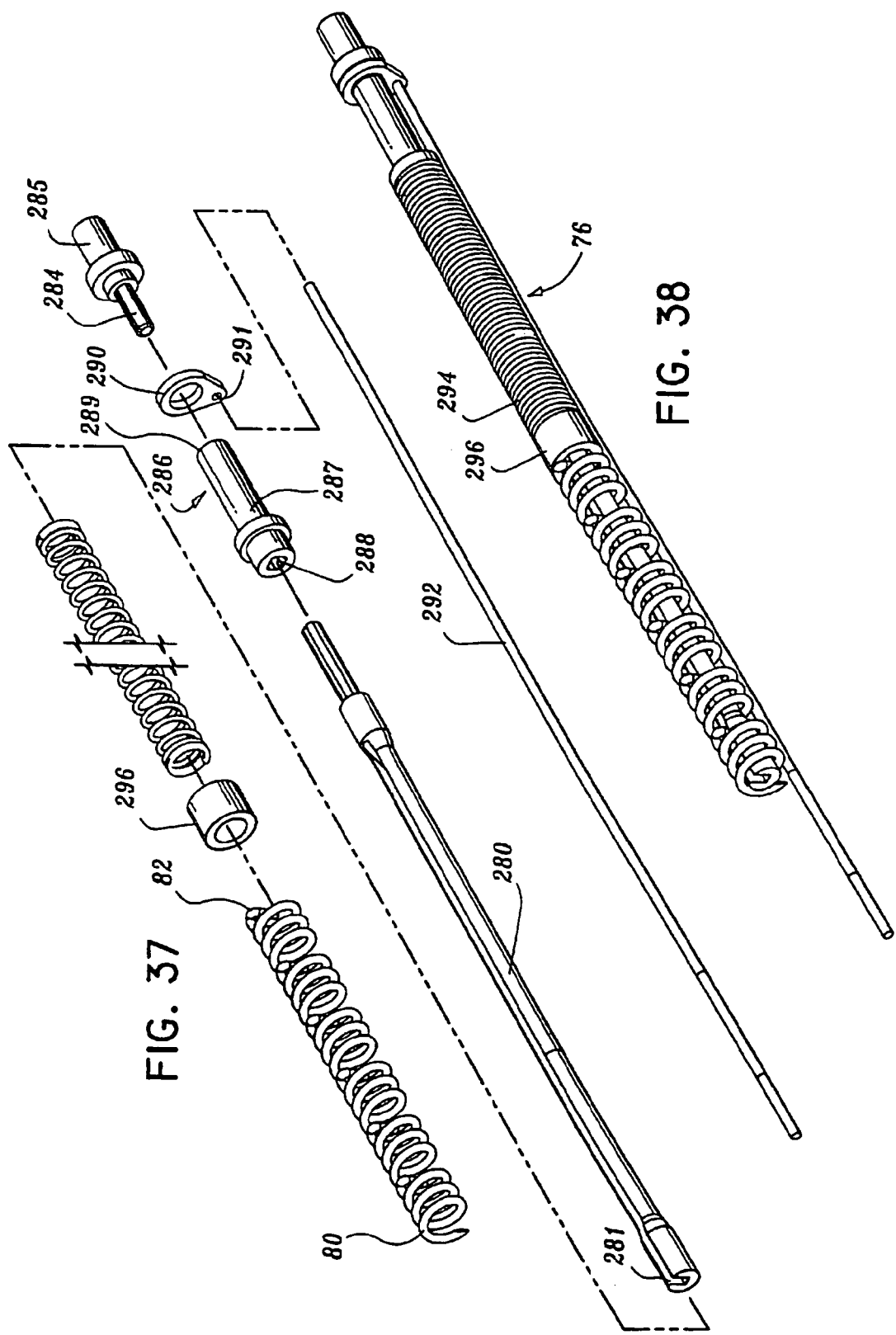

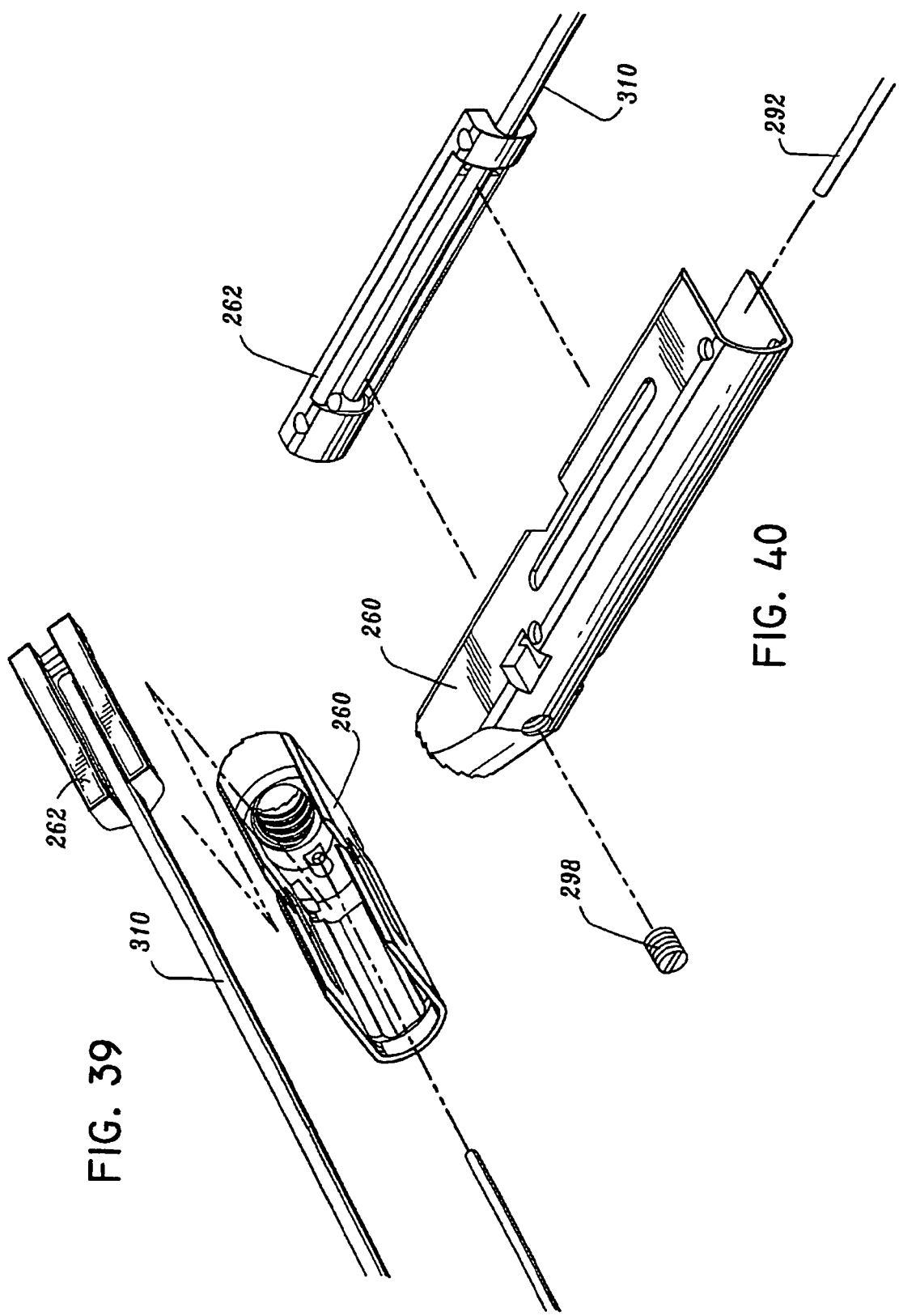

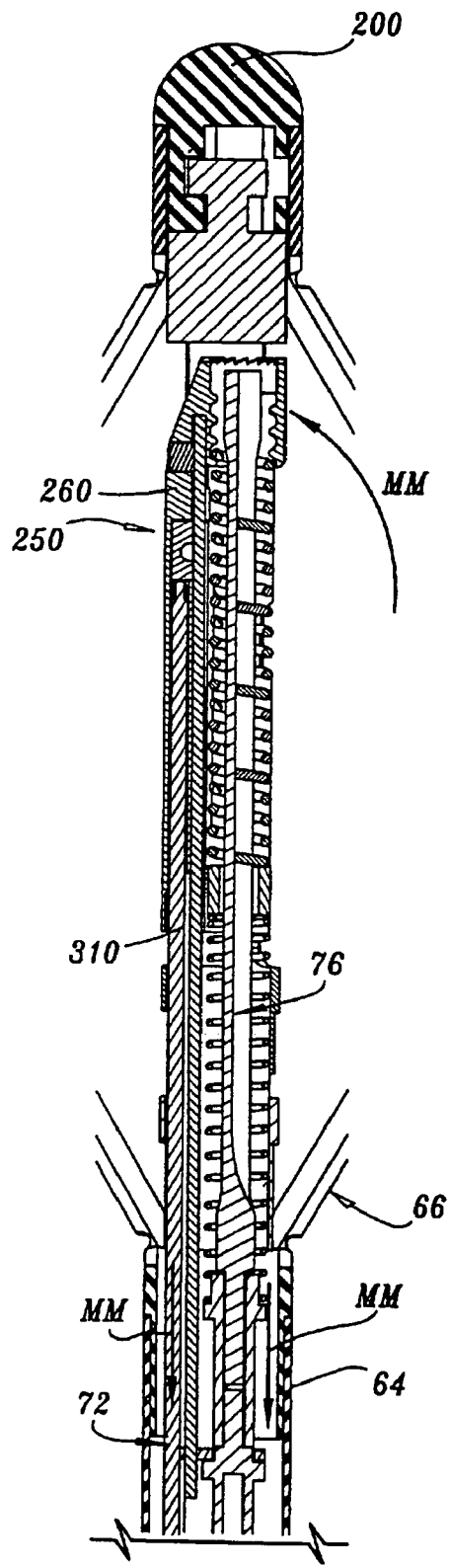
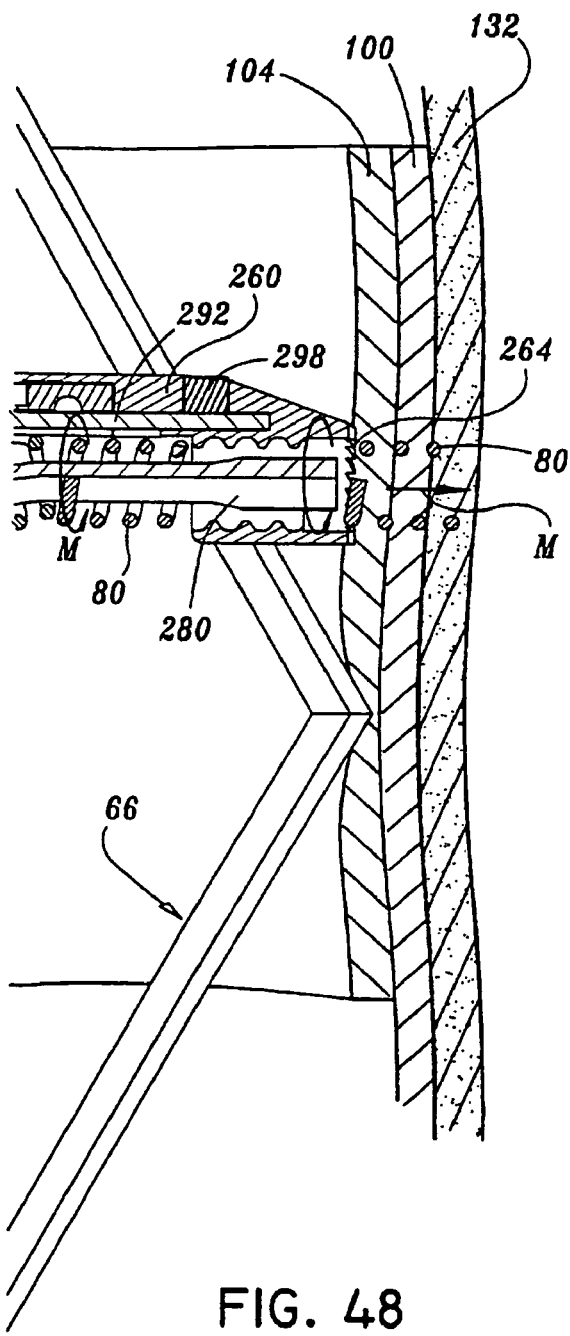
FIG. 48
FIG. 49

SYSTEMS AND METHODS FOR APPLYING A SUTURE WITHIN A BLOOD VESSEL LUMEN

RELATED APPLICATION

This application is a divisional of U.S. Pat. application Ser. No. 10/099,149 filed 15 Mar. 2002 now U.S. Pat. No. 6,800,081, which is a divisional of application Ser. No. 09/787,135, filed Jun. 4, 2001, entitled "Endovascular Fastener Applicator," now U.S. Pat. No. 6,592,593, which claims the benefit of U.S. Provisional Application Ser. No. 60/101,050 filed Sep. 18, 1998.

FIELD OF THE INVENTION

This disclosure relates generally to vascular grafts for intraluminal delivery, and in particular, to a method and apparatus for repairing diseased or damaged sections of a vessel by fastening a prosthesis within the vessel.

BACKGROUND OF THE INVENTION

Diseased or damaged blood vessels often cause weakening of the vessel wall resulting in an aneurysm whereby a blood vessel and especially an artery have a section of abnormal blood-filled dilation. For example, an abdominal aortic aneurysm is a sac caused by an abnormal dilation of the wall of the aorta, a major artery of the body as it passes through the abdomen.

The abdominal aortic aneurysm usually arises in the infrarenal portion of the arteriosclerotically diseased aorta, for example, below the kidneys. Left untreated, the aneurysm will eventually cause rupture of the sac with ensuing fatal hemorrhaging in a very short time. High mortality associated with rupturing led the state of the art into trans-abdominal surgical repair of abdominal aortic aneurysms.

Surgery involving the abdominal wall, however, is a major undertaking with associated high risks. This type of surgery, in essence, involves replacing the diseased and aneurysmal segment of blood vessel with a prosthetic device which typically is a synthetic tube, or graft, usually fabricated of either DACRON™, TEFLON™, or other suitable material.

The present state of the art for intraluminal repair of a vessel does not fasten a prosthesis to the remaining aortic wall. For example, U.S. Pat. Nos. 5,571,171 and 5,571,173 disclose a method and apparatus for treating an abdominal aortic aneurysm by supplying a prosthesis or an aortic graft for intraluminal delivery that does not fasten the graft to the remaining aortic wall.

Presenting an aortic graft through the aorta by intraluminal delivery avoids major invasive surgery. The '171 and '173 patents disclose an aortic graft that is delivered intraluminally to the aneurysm site. The aortic graft is secured to the remaining aortic wall by a balloon that is inflated thereby causing the graft to contact and adhere to the remaining aortic wall.

The major disadvantages related to the combination of endovascular expanders, such as a balloon or stent, and prosthesis is the dilation of the natural artery with consequent migrations and periprosthetic losses. Upon withdrawal of the expander, the tissue is caused to collapse and the prosthesis disengages from the remaining aortic wall and tends to migrate to a location away from the aneurysm site to be repaired. The migration and movement of the disengaged aortic graft would then obstruct the affected vessel. The migration and movement of the aortic graft requires further treatment on the patient to remove the failed attempt to attach the aortic graft to the remaining aortic wall.

Further treatment may include major surgery that is hazardous and traumatic to the patient. Major surgery to remove the aortic graft defeats the benefits of intraluminal delivery of the aortic graft. The current state of the art does not disclose a fastener applicator that intraluminally delivers a vascular graft and endoluminally applies internal fasteners to fasten a prosthesis in place.

Accordingly, there is a present need for a fastener applicator that intraluminally delivers a vascular graft to a site within a vessel and applies fasteners to pass through both a prosthesis and the thickness of a vessel wall. The fastened prosthesis should also have the capability of following dilation of a vessel.

SUMMARY OF THE INVENTION

The invention provides systems and methods for applying a suture within a blood vessel lumen. The systems and methods advance within a blood vessel lumen a catheter tube having a distal region that carries a suture applicator. The systems and methods operate the suture applicator from a location external to the blood vessel lumen to apply a suture to an interior wall of a blood vessel lumen.

Other features and advantages of the invention will be pointed out in, or will be apparent from, the drawings, specification and claims that follow.

DESCRIPTION OF THE DRAWINGS

FIG. 11 is a cross-sectional view of the control assembly;

FIG. 12 is a cross-sectional view, in part elevation, of the applicator at the aneurysm site showing an expandable portion causing a prosthesis to contact a vessel wall;

FIG. 13 is a cross-sectional view of the control assembly;

FIG. 14 is a cross-sectional view, in part elevation, of the applicator at the aneurysm site showing advance of a delivery tube;

FIG. 15 is a cross-sectional view of the control assembly;

FIG. 16 is a cross-sectional view, in part elevation, of the applicator at the aneurysm site showing advance of a drive assembly;

FIG. 29 is a perspective view of the distal end of an alternate embodiment of the drive assembly loaded with a plurality of helical fasteners;

FIG. 30 is a perspective view showing a helical fastener for loading with a channel of the drive assembly;

FIG. 31 is a perspective view of an alternate embodiment of a helical fastener;

FIG. 34 is a perspective view of an alternate embodiment of the applicator showing the expandable portion in an expanded state;

FIG. 35 is a perspective view of the expandable portion shown in FIG. 34 in a relaxed state;

FIG. 37 is an exploded view of the drive assembly shown in FIG. 34;

FIG. 38 is a perspective view of the drive assembly shown in FIG. 34;

FIG. 39 is a perspective view of an embodiment of an ejection mount;

FIG. 40 is a perspective view of the ejection mount showing a set screw and cam divider for cooperating with the drive assembly;

FIG. 48 is a perspective view, in part cross-section, showing deployment of helical fasteners;

FIG. 49 is a perspective view, in part cross-section, showing retraction of the ejection mount;

Figure 1:
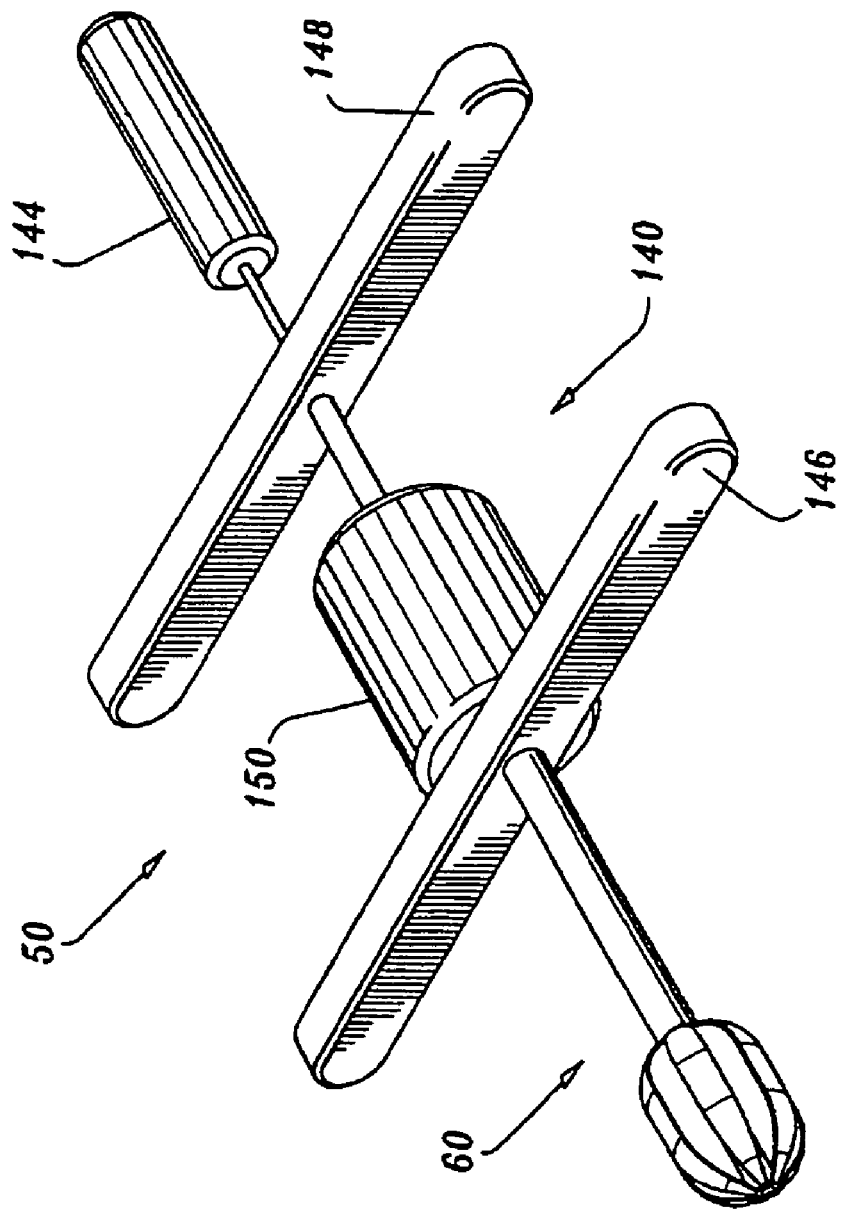
FIG. 1 is a perspective view of one embodiment of an endovascular fastener applicator in accordance with the present disclosure.

The invention is not limited to the details of the construction and the arrangements of parts set forth in the following description or shown in the drawings. The invention can be practiced in other embodiments and in various other ways. The terminology and phrases are used for description and should not be regarded as limiting.

DESCRIPTION OF THE PREFERRED EMBODIMENTS

Figures 2, 3:
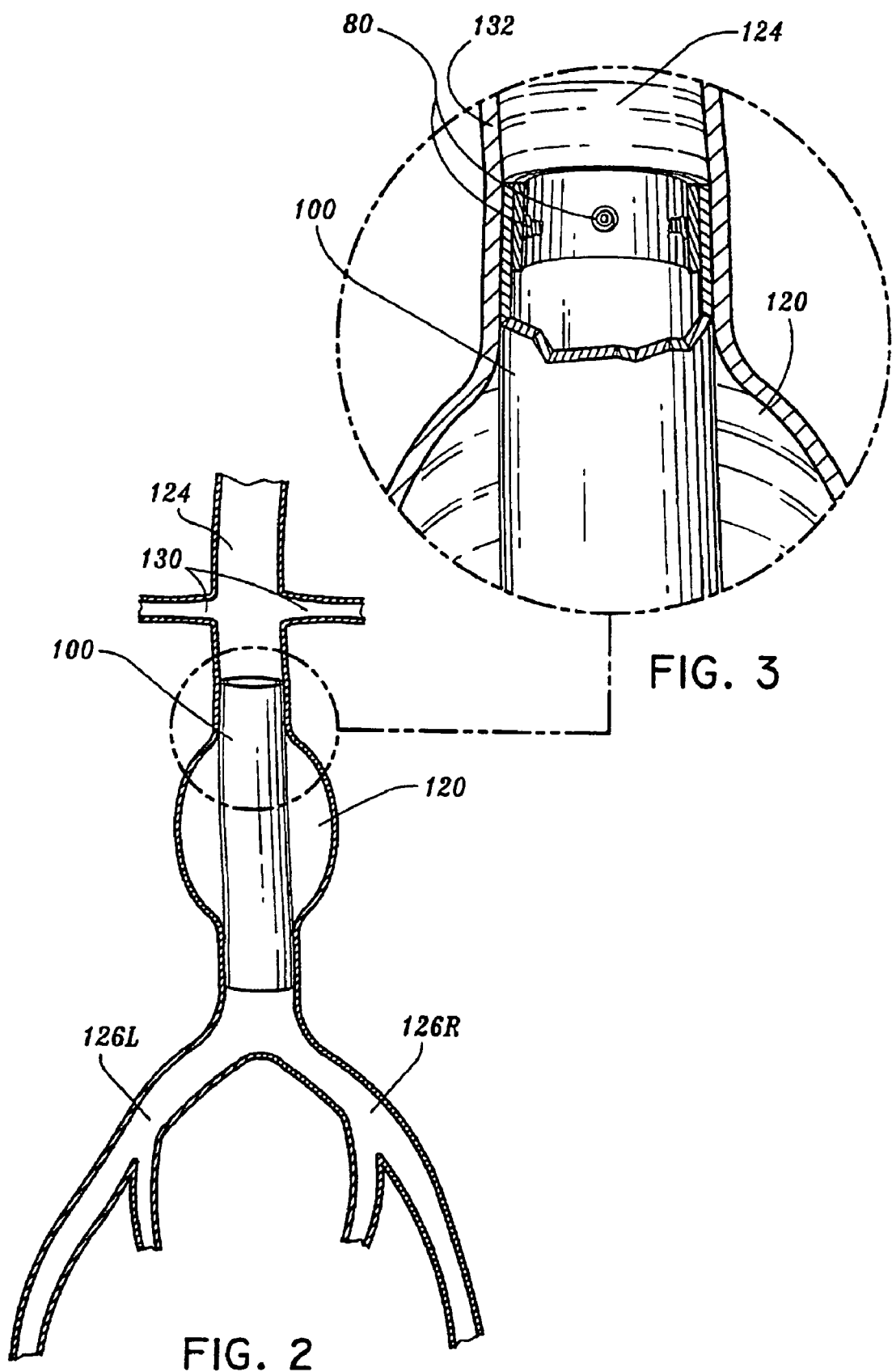
FIG. 2 is a cross-sectional view, in part elevation, of an aortic graft placed at the site of all abdominal aortic aneurysm within the aorta.
FIG. 3 is an enlarged detail view of a portion of FIG. 2 illustrating the aortic graft secured to the remaining aortic wall and maintained in position by helical fasteners.
Figure 4:
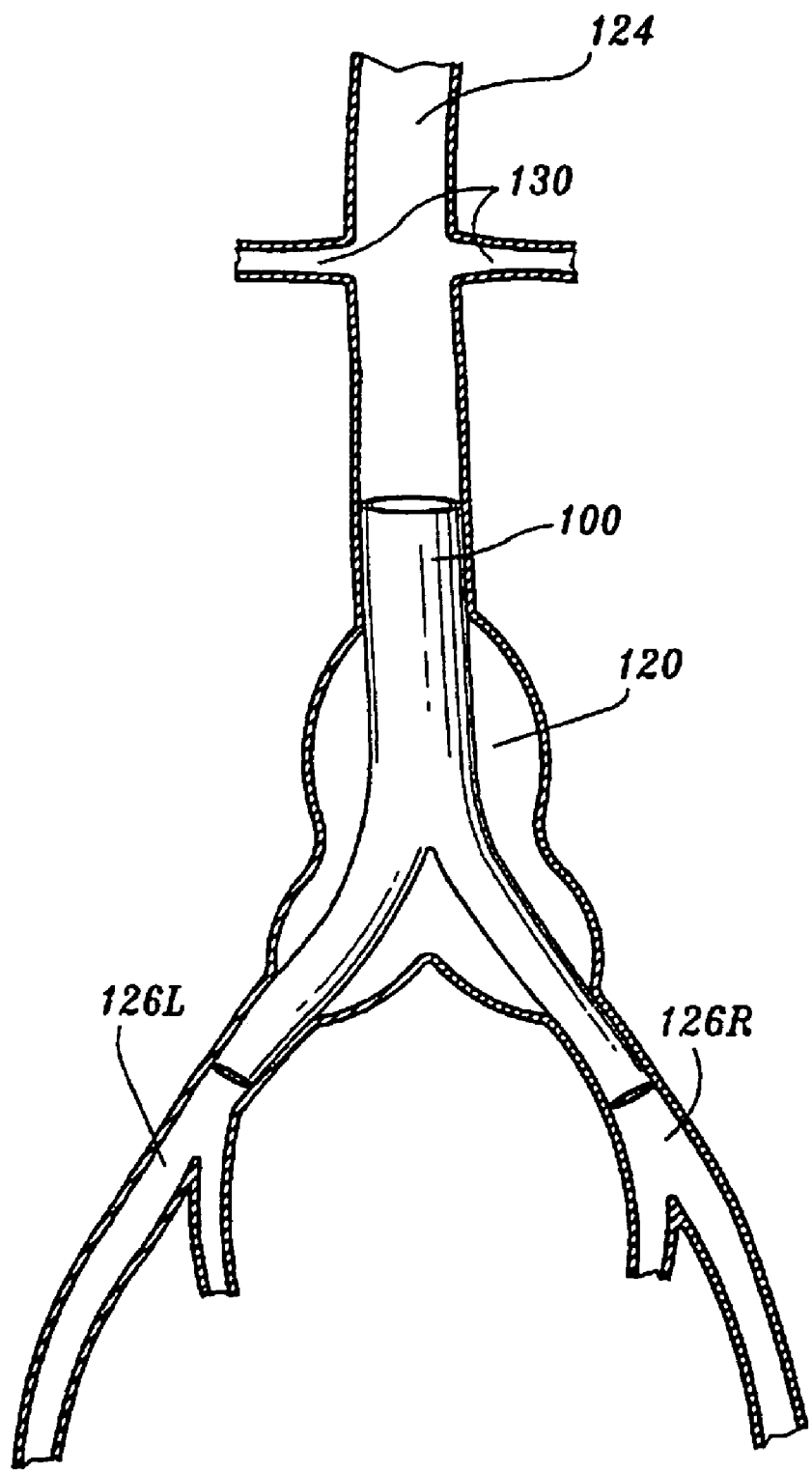
FIG. 4 is a cross-sectional view, in part elevation, of an aortic graft for treating an aortic aneurysm affecting the aorta and both ileac arteries.
Figure 7:
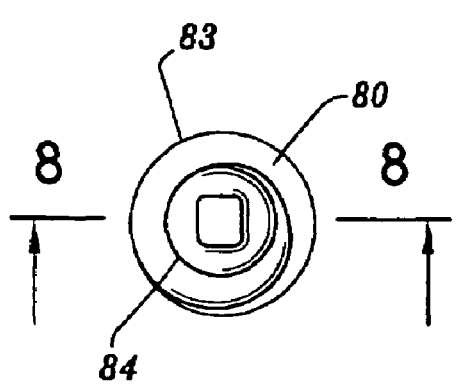
FIG. 7 is a bottom perspective view taken along line 7-7 of FIG. 6 of a helical fastener having a rectangular configuration at its limiting end for cooperating with a rectangular drive assembly.
Figure 5:
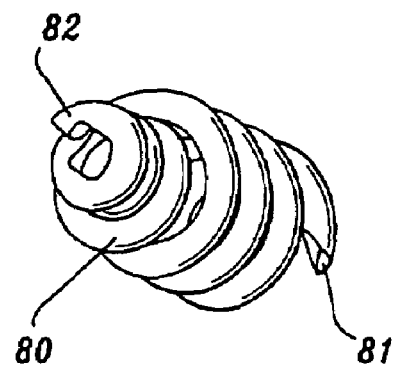
FIG. 5 is a perspective view of a helical fastener.
Figure 6:
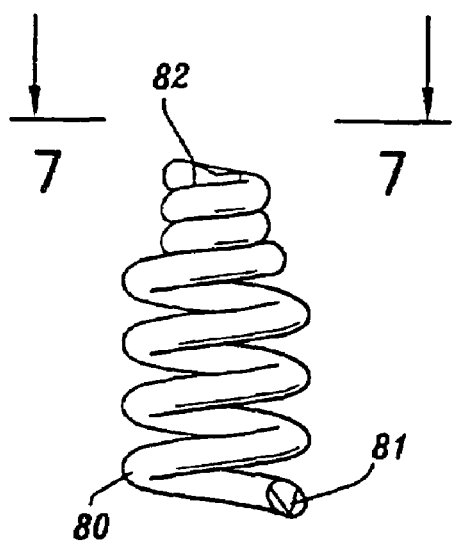
FIG. 6 is a side elevation view of a helical fastener.
Figure 8:
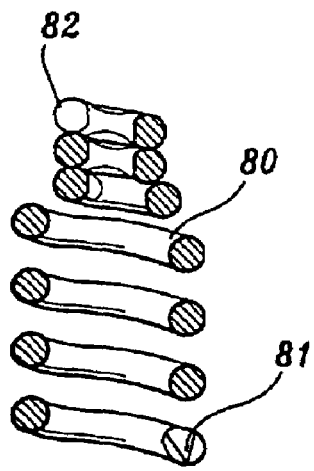
FIG. 8 is a cross-sectional view taken along line 8-8 of FIG. 7 of a helical fastener.

As illustrated in FIG. 1, the present disclosure relates to an endovascular fastener applicator, generally referred to as numeral 50. Endovascular fastener applicator 50 delivers aortic graft 100, as shown in FIGS. 2 and 3, for repairing an abdominal aortic aneurysm 120 in aorta 124 having two iliac arteries 126L and 126R associated therewith, as well as a plurality of renal arteries 130 located above aneurysm 120 in fluid communication with aorta 124. Repairing the aneurysm includes fastening an aortic graft 100 to an aortic wall 132 by fasteners 80. Aortic graft 100, as well as other prostheses, may be utilized in the thoracic aorta, and can be used to repair thoracic aneurysms or thoracic dissecting aneurysms. Further, the fastener applicator 50 may also treat vascular trauma and other obstructive diseases with various prostheses. Accordingly, use of the term aortic aneurysm in this specification and claims is intended to relate to and mean both abdominal aortic aneurysms, thoracic aneurysms and related vessel diseases.

Figure 9:
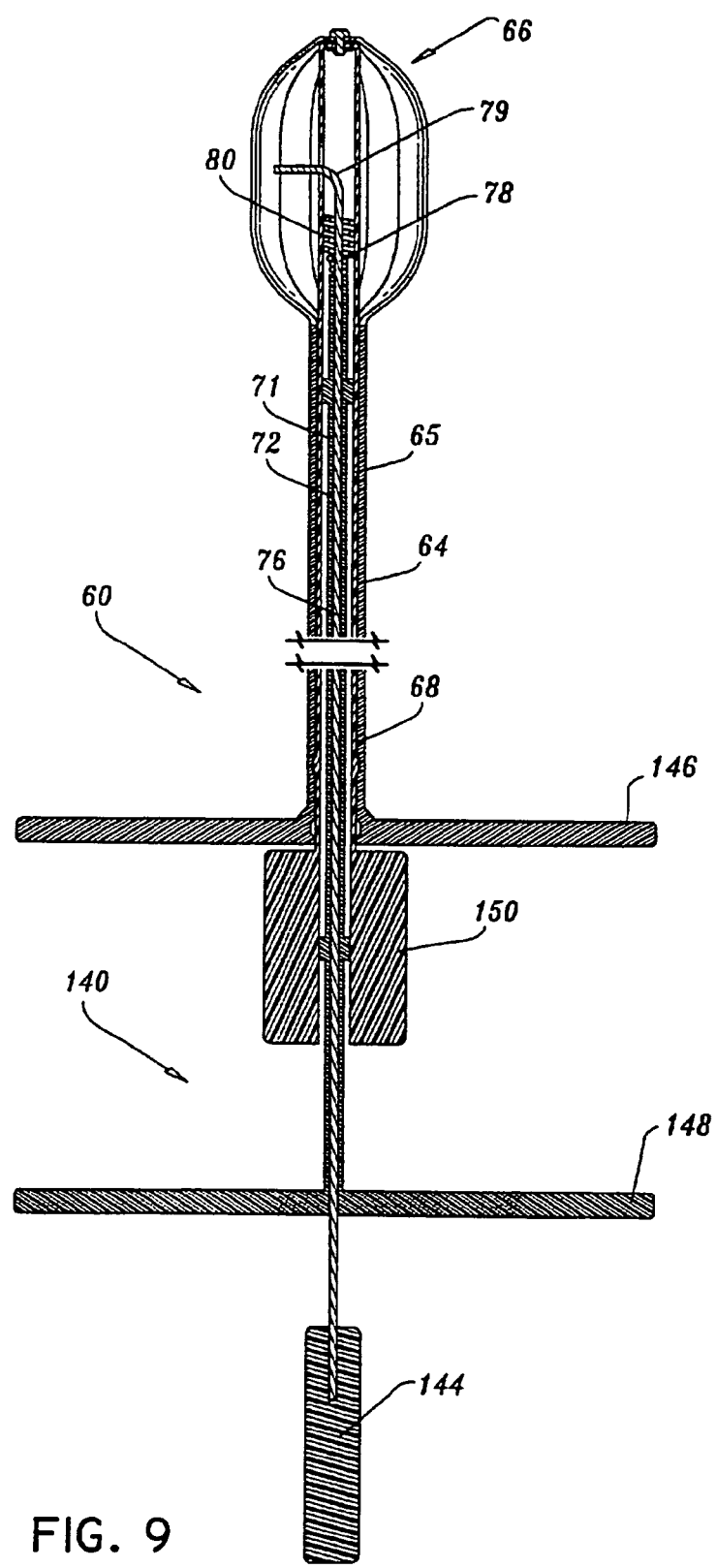
FIG. 9 is a cross-sectional view, in part elevation, of an endovascular fastener applicator.
Figure 10:
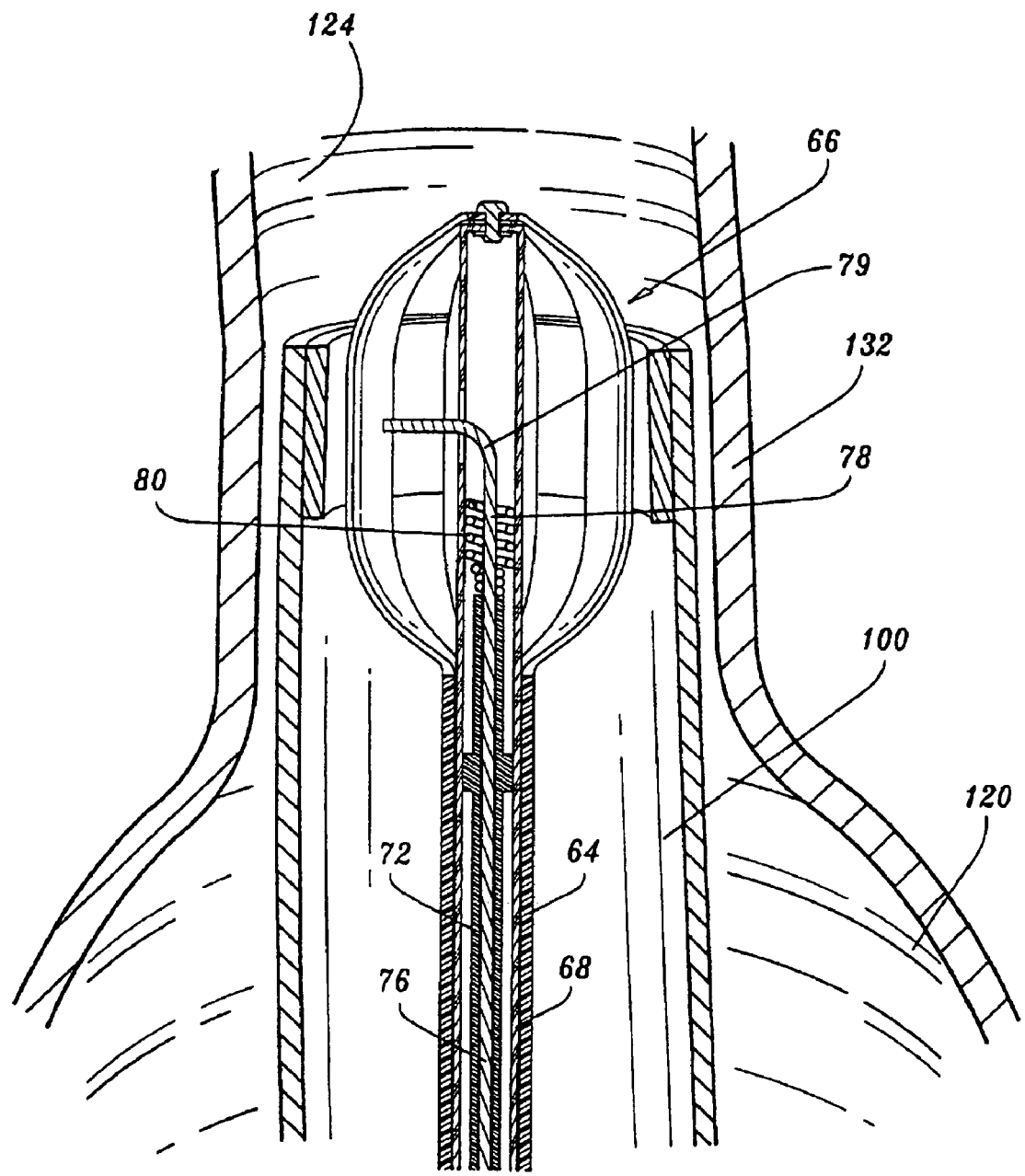
FIG. 10 is a cross-sectional view, in part elevation, of a distal portion of the applicator at the aneurysm site.

Endovascular fastener applicator 50 has a delivery assembly 60 and a control assembly 140. Delivery assembly 60, as illustrated in FIG. 9, includes a tubular body, such as, for example, an outer sleeve 64, an elongate control 68, a delivery tube 72 and a drive assembly 76, each having a proximal and distal end relative to control assembly 140. Outer sleeve 64 defines a channel 65 and is adapted for insertion within aorta 124 (as shown in FIG. 10) and has an expandable portion 66 operatively connected at its distal end. Elongate control 68 is coaxially positioned within channel 65 of outer sleeve 64 and is operatively connected to expandable portion 66 at its distal end. Delivery tube 72 defines a channel 71 and is coaxially positioned within channel 65 of outer sleeve 64 and adapted for advancing a helical fastener 80 to the abdominal aortic aneurysm site. Drive assembly 76 is coaxially positioned within channel 71 of delivery tube 72 and adapted for advancing, in cooperation with delivery tube 72, and deploying helical fastener 80 into aortic graft 100 and aorta wall 132. It is contemplated that the components of the delivery assembly may be alternately oriented relative to each other, such as, for example, bi-axial, offset, etc. It is further contemplated that the components of delivery assembly 60 are flexible and may be constructed from a shape memory material.

Operation of endovascular fastener applicator 50 is controlled by control assembly 140. As shown in FIGS. 1 and 9, control assembly 50 includes outer sleeve push bar 146, expandable portion control 150, delivery tube push bar 148 and handle 144. Outer sleeve push bar 146 is operatively connected to the proximal end of outer sleeve 64 for regulating movement of outer sleeve 64. Expandable portion control 150 is operatively connected to the proximal end of elongate control 68, which in turn is connected to expandable portion 66. Correspondingly, expandable portion control 150 controls the expansible force AA (shown in FIG. 12) exerted by expandable portion 66 for supporting aortic graft 100 in contact with aortic wall 132. Outer sleeve push bar 146 may also be adapted to influence expansible force AA.

Delivery tube push bar 148 is operatively connected to the proximal end of delivery tube 72 for regulating movement of delivery tube 72. Handle 144 is operatively connected to the proximal end of drive assembly 76, for controlling axial and rotational movement of drive assembly 76, described in detail below.

As shown in FIG. 9, drive assembly 76 includes a drive 78. Drive 78 at its distal end has a curved portion 79 oriented at substantially 90' to the longitudinal axis of outer sleeve 64 and delivery tube 72 (similarly shown in FIGS. 10 and 12). It is contemplated that the curved portion may be positioned at various angular orientations. Drive assembly 76 transmits rotational motion from its proximal end to its distal end and through its curved portion 79 to facilitate deployment of helical fasteners 80 into the aortic graft 100 and aortic wall 132.

In one embodiment, as illustrated in FIGS. 5-8, helical fasteners 80 have a sharpened distal end 81 and a penetration limit end 82. Helical fastener 80 has an outer diameter 83 and an inner diameter 84. Outer diameter 84 facilitates penetration of sharpened distal end 81 into aortic graft 100 and aortic wall 132. The surface of inner diameter 84 cooperatively engages drive assembly 76 and delivery tube 72 at their distal ends to facilitate loading of helical fastener 80 into endovascular fastener applicator 50. Preferably, inner diameter 84 and penetration limit end 82 have a rectangular configuration for cooperative engagement with drive assembly 76, drive assembly 76 also having a rectangular configuration at its distal end. Although a helical fastener is disclosed it is contemplated that fastener 80 may have various configurations, such as, for example, cylindrical, triangular, etc. It is further contemplated that fasteners 80 are of the metallic fastener staple type and are preferably made from stainless steel but may be constructed from a polymeric material.

Figure 19:
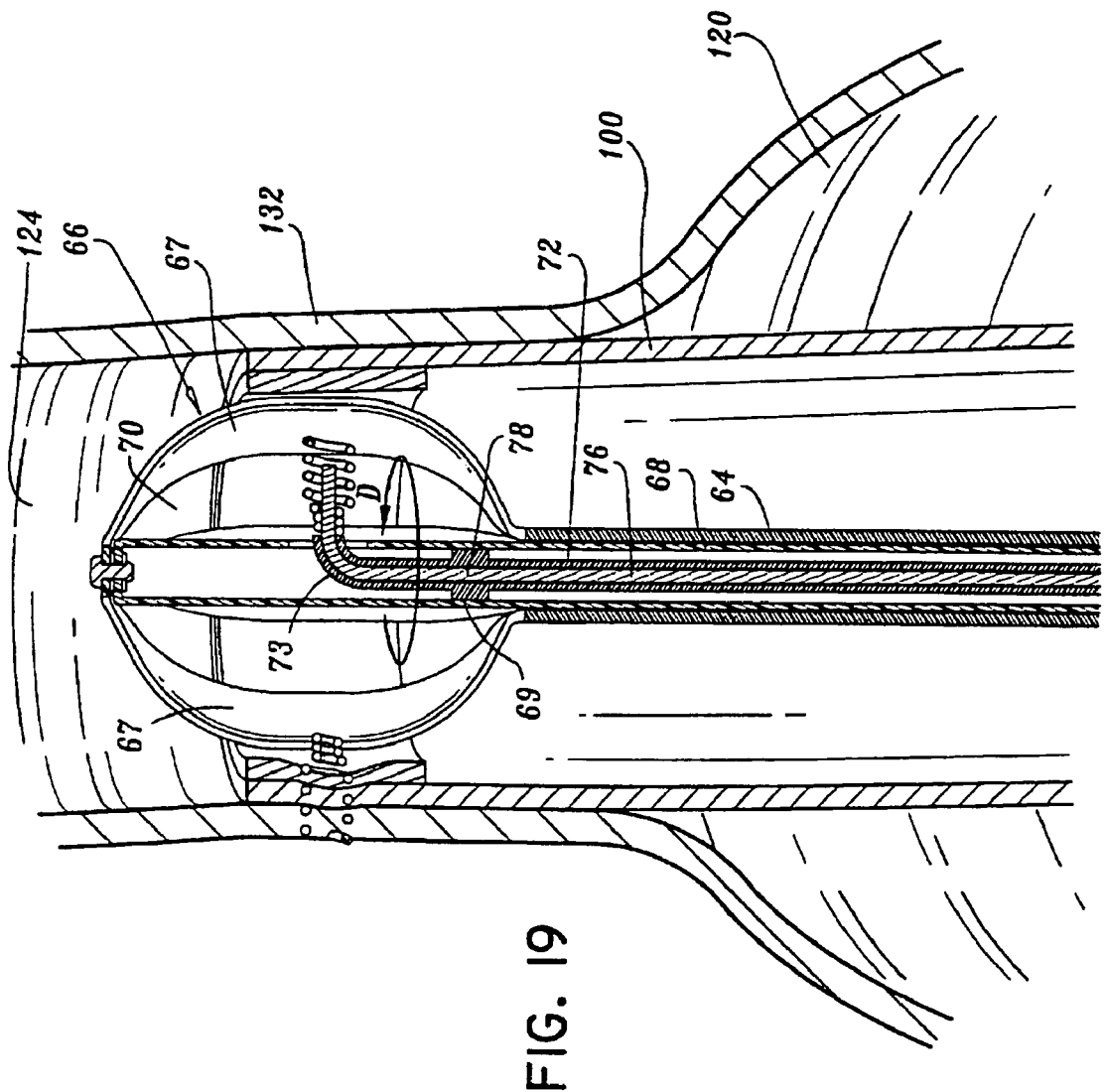
FIG. 19 is a cross-sectional view, in part elevation, of the delivery assembly showing rotation for insertion of a helical fastener.

In the embodiment illustrated in FIG. 9, drive 78 is made from a shape memory alloy whereby drive 78 assumes the curved configuration of curved portion 79 upon exiting delivery tube 72. Delivery tube 72 may also include an applicator head 73 at its distal end having a curved orientation to facilitate deployment of helical fasteners 80, as shown in FIGS. 14, 16 and 19. Helical fasteners 80, as shown in FIG. 3, are deployed into aortic graft 100 and aortic wall 132 for fastening.

In an alternate embodiment, repair of abdominal aortic aneurysm 120, as shown in FIG. 10, proceeds by insertion of endovascular fastener applicator 50 into aorta 124 and advancing to the abdominal aortic aneurysm site by manipulation by a surgeon of control assembly 140. Endovascular fastener applicator 50 delivers aortic graft 100 to abdominal aortic aneurysm 120 by advancing the aortic graft 100 so that a sufficient portion of aortic graft 100 is brought in contact with aortic wall 132. Aortic graft 100 is a conventional tubular graft made of DACRON®, TEFLONV (polytetrafluoroethylene) and the like and is of a length sufficient to span the abdominal aortic aneurysm 120.

With reference to FIGS. 11-19, delivery assembly 60 and aortic graft 100 are delivered to the abdominal aneurysm site by manipulation of outer sleeve push bar 146, as shown by arrows A in FIG. 11. Aortic graft 100 is positioned at the abdominal aneurysm site. Expandable portion 66 is caused to expand, shown by arrows AA in FIG. 12, in response to cooperative manipulation of outer sleeve push bar 146 and elongate control 68. Outward radial force AA supports aortic graft 100 in contact with aortic wall 132. Expandable portion 66 facilitates fastening of aortic graft 100 with aortic wall 132 by deployment of helical fasteners 80. In this embodiment, expandable portion 66 includes support members 67 that define interstitial regions 70 therebetween. Helical fasteners 80 are deployed through interstitial regions 70 and into aortic graft 100. It is contemplated that helical fasteners 80 may be deployed at various locations about the circumference of aortic graft 100 relative to the number of support members 67 and spacing of interstitial regions 70.

Delivery tube push bar 148 is manipulated to axially advance delivery tube 72 within outer sleeve 64, as shown by arrows B in FIG. 13. At its distal end, delivery tube 72 has an applicator head 73 configured to have a substantially perpendicular orientation to the longitudinal axis of delivery tube 72. Drive 78 follows the substantially perpendicular orientation of delivery tube 72 to facilitate deployment of helical fasteners 80. It is contemplated that applicator head 73 may have various configurations and orientations to facilitate deployment of helical fasteners 80.

With reference to FIG. 14, delivery tube 72 is advanced to a location where aortic graft 100 will be fastened to aortic wall 132. A loaded helical fastener 80 is oriented for deployment by applicator head 73, as shown by arrows C. Applicator head 73 is articulable in a clockwise and a counter-clockwise direction about the inner surface of graft 100.

Figure 17:
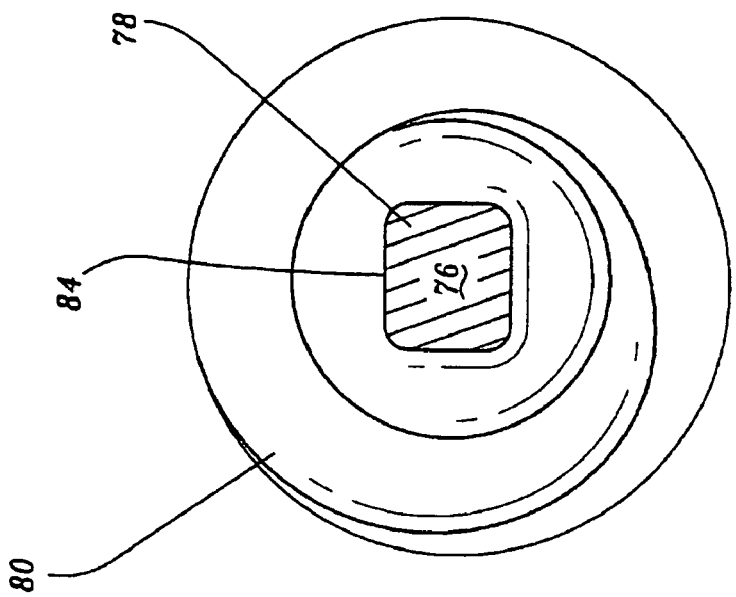
FIG. 17 is a top view of a helical fastener defining a rectangular configuration at its limiting end for cooperating with a rectangular drive assembly, as shown in cross-section.

The surface of inner diameter 84 and penetration limit end 82 of helical fastener 80 have a rectangular configuration for cooperative engagement with drive assembly 76, drive assembly 76 also having a rectangular configuration at its distal end (FIG. 17).

It is contemplated that the remainder of drive assembly 76 may not be in cooperative engagement with the surface of inner diameter 84.

Helical fastener 80 has a substantially circular cross-section. It is envisioned that other cross-sectional configurations may be used that are suitable for fastening.

With reference to FIGS. 15 and 16, handle 144 is manipulated to advance drive assembly 76. A torque is applied to handle 144 transmitting a rotational force from the proximal end to the distal end of drive assembly 76. The rectangular configuration of drive assembly 76 cooperates with the rectangular configuration of the surface of inner diameter 84 causing rotational movement of helical fastener 80. The sharpened distal end 81 of helical fastener 80 contacts the interior wall 102 of aortic graft 100 thereby facilitating deployment of fastener 80 into aortic graft 100 and aortic wall 132. Helical fastener 80 penetrates aortic graft 100 and aortic wall 132 to penetration limit end 82 thereby fastening aortic graft 100 to aortic wall 132.

Figure 18:
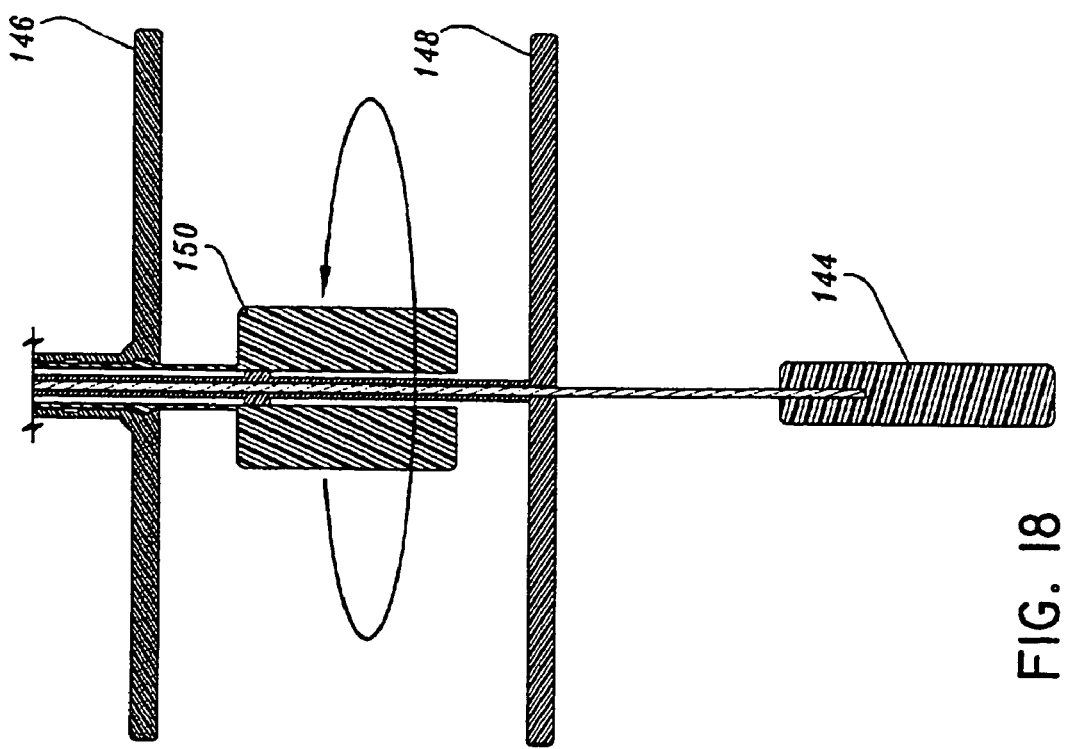
FIG. 18 is a cross-sectional view of the control assembly.

In the embodiment shown in FIG. 19, delivery tube 72 cooperates with elongate control 68 at junction 69. Junction 69 facilitates rotation of delivery tube 72 and drive assembly 76 positioned coaxially therewithin, to a location for deployment of helical fasteners 80, as shown in FIG. 19 by arrow D. Junction 69 rotates by manipulation of expandable portion control 150, as shown in FIG. 18. Delivery tube 72 is retracted from the fastening site and loaded with another helical fastener 80 for subsequent deployment at another location along the diameter of aortic graft 100. As many helical fasteners 80 may be deployed as are necessary to adequately fasten aortic graft 100 to aortic wall 132. Fastening in this manner prevents periprosthetic losses and accidental migration of aortic graft 100. It is contemplated that multiple helical fasteners 80 may be loaded into endovascular fastener applicator 50.

Figure 20:
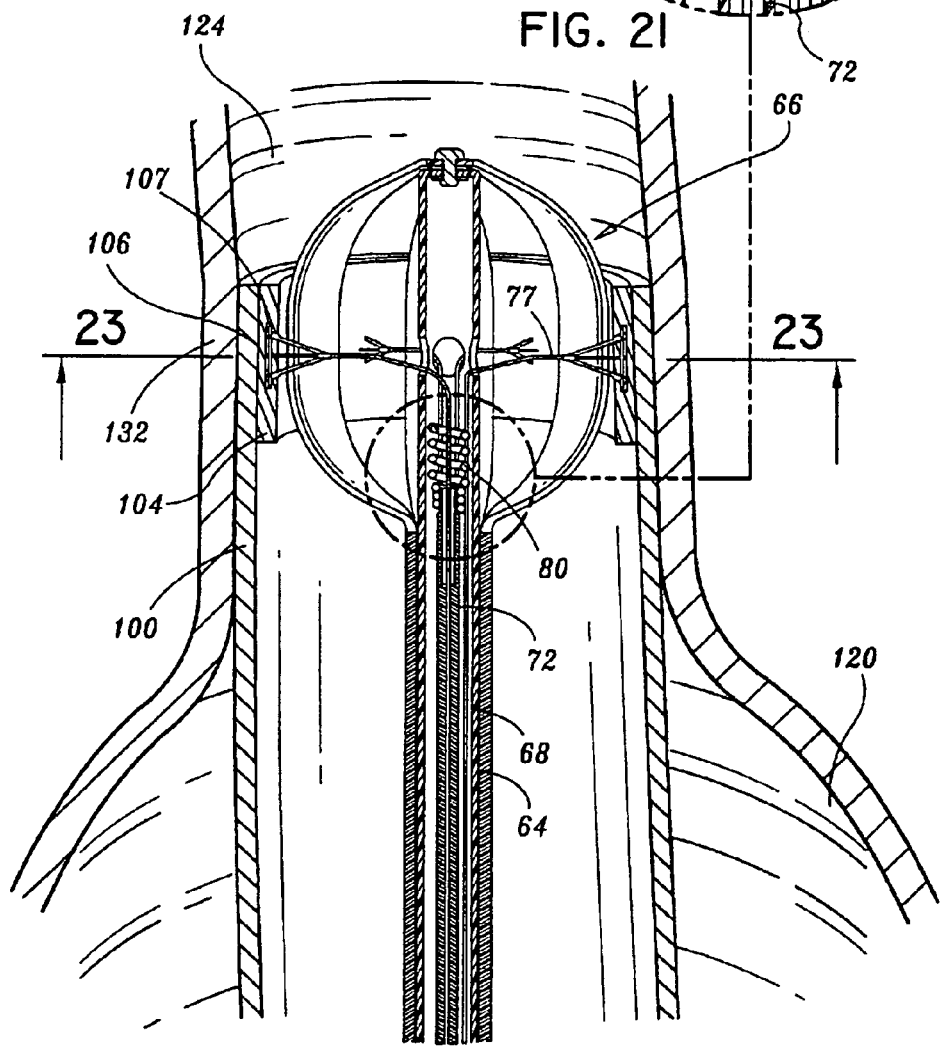
FIG. 20 is a cross-sectional view, in part elevation, of an alternate embodiment of the applicator showing the delivery assembly at the aneurysm with fastener guides.

In another embodiment, as shown in FIGS. 20-27, endovascular fastener applicator 50 positions aortic graft 100 at the aneurysm site and in contact with aortic wall 132. Referring to FIG. 20 aortic graft 100 includes band 104 having anchor pads 107 implanted therewithin.

Figure 23:
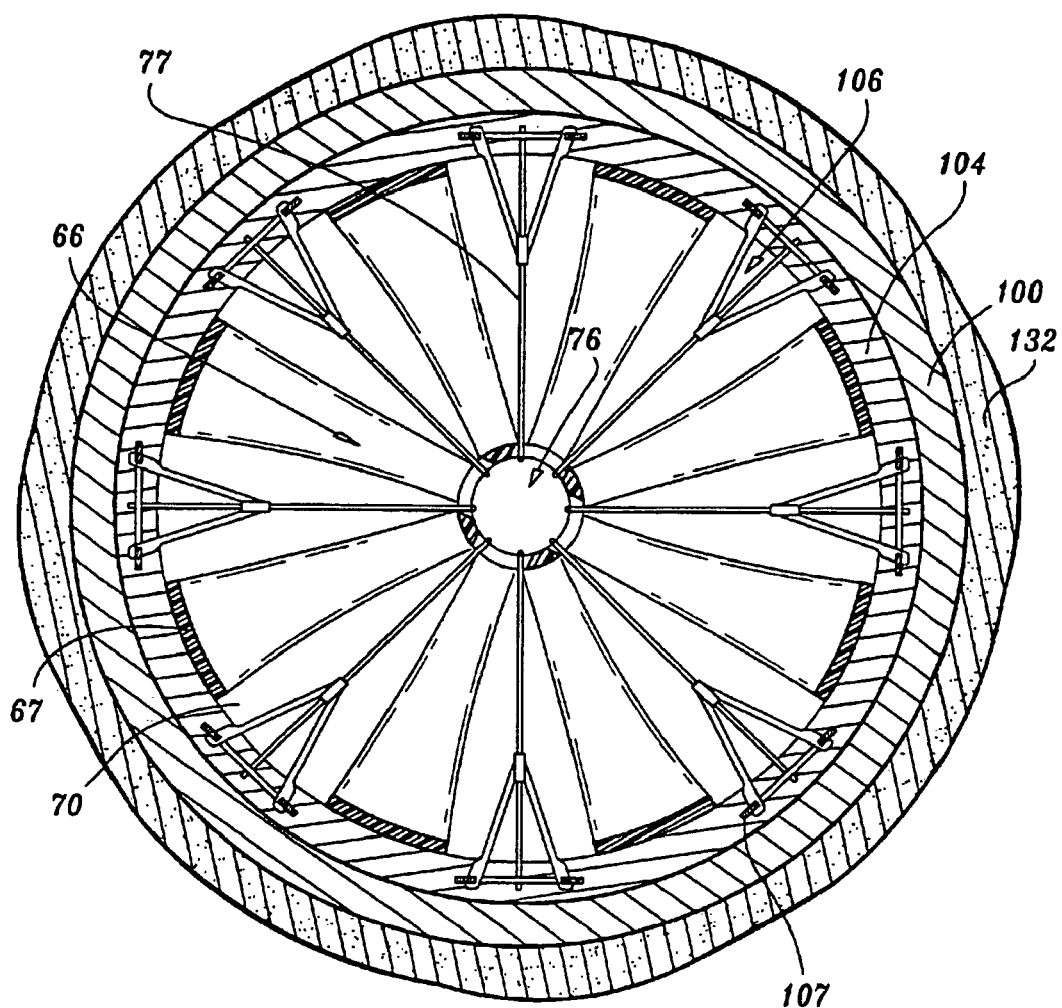
FIG. 23 is a plan view, in part cross-section, taken along line 23-23 of FIG. 20 showing the applicator with fastener guides.
Figure 24:
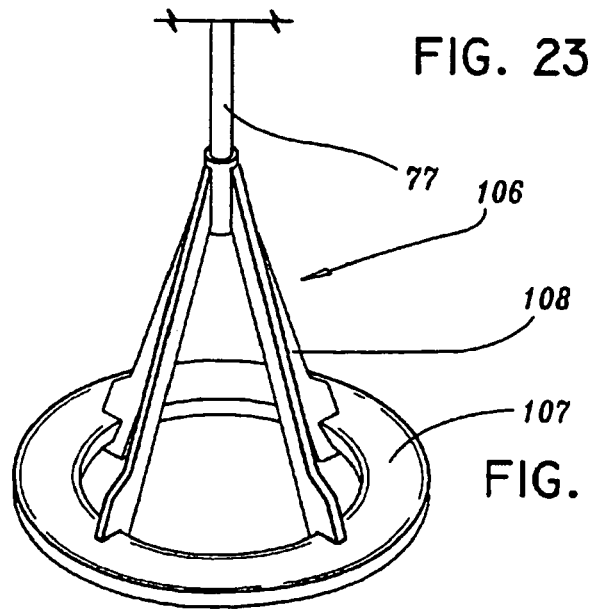
FIG. 24 is a perspective view of one embodiment of a fastener guide in accordance with the present disclosure.

As shown in FIG. 23, anchor pads 107 are implanted circumferentially about band 104. Band 104 may be fabricated from, such as, for example, polytetrafluoroethylene. Anchor pads 107, are implanted within band 104 corresponding to interstitial regions 70 located between support members 67 of expandable portion 66. Referring to FIG. 23, pads 107 have a substantially circular configuration. It is envisioned that the pads may have other configurations such as, for example, rectangular, elliptical, etc.

Figure 22:
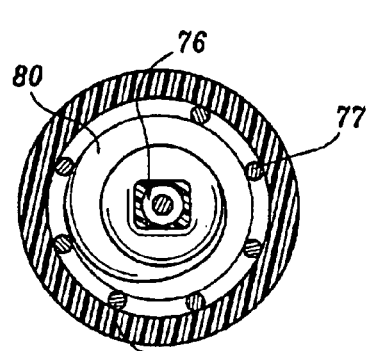
FIG. 22 is a cross-sectional view, in part elevation, of a helical fastener taken along line 22-22 of FIG. 21.
Figure 21:
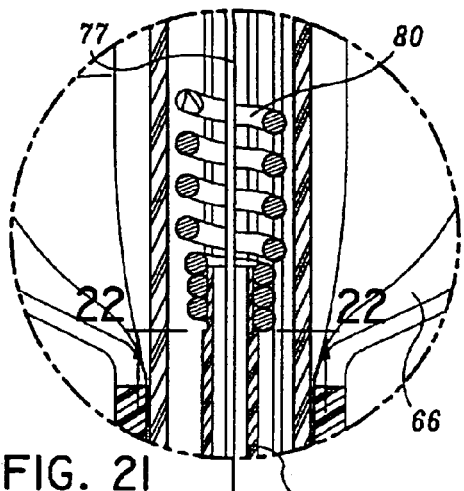
FIG. 21 is an enlarged detail view of a portion of FIG. 20 illustrating a helical fastener guided over a drive attached to a fastener guide.

Anchor pads 107 cooperatively engage fastener guides 106 positioned at the distal end of drive assembly 76. Anchor pads 107 and fastener guides 106 cooperate to provide a guided deployment of helical fasteners 80 and facile release of drive assembly 76 from the aneurysm site. Referring to FIGS. 21 and 22, drive assembly 76 further includes multiple guide wires 77 releasably attached to fastener guides 106. Guide wires 77 facilitate guided travel of fasteners 80.

Referring back to FIG. 24, fastener guides 106 include anchor legs 108. Anchor legs 108 are resiliently biased so that upon deployment of helical fastener 80, anchor legs 108 are caused to collapse and release from band 104. Anchor legs 108 are connected to multiple guide wires 77 so that after collapse and release of anchor legs 108, multiple guide wires 77 are retracted from the fastening site. Anchor pad 107 is retained within band 104 after helical fastener 80 is deployed.

Figure 25:
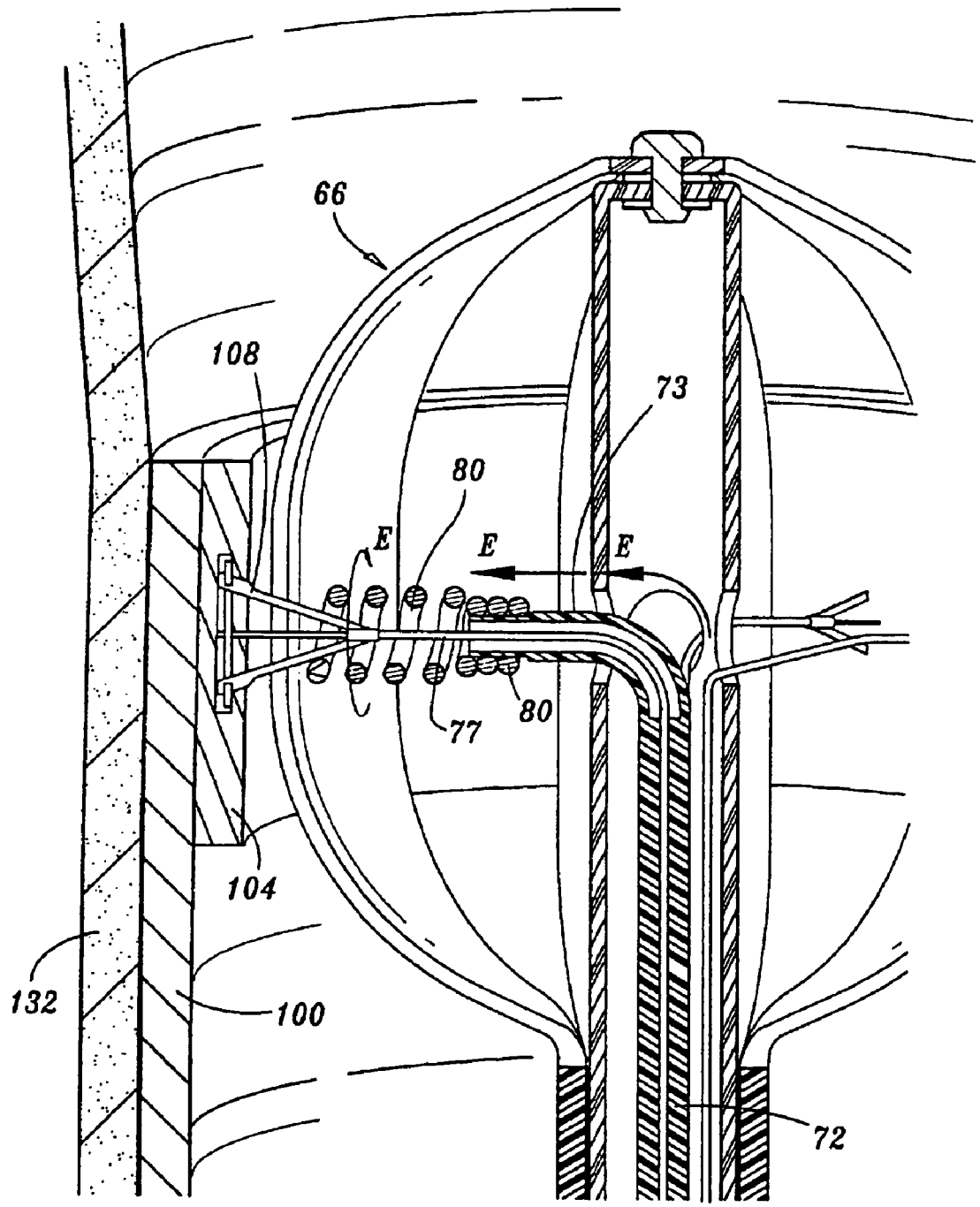
FIG. 25 is a perspective view, in part cross-section, showing movement of the helical fastener over a drive prior to collapsing the fastener guide.
Figure 26:
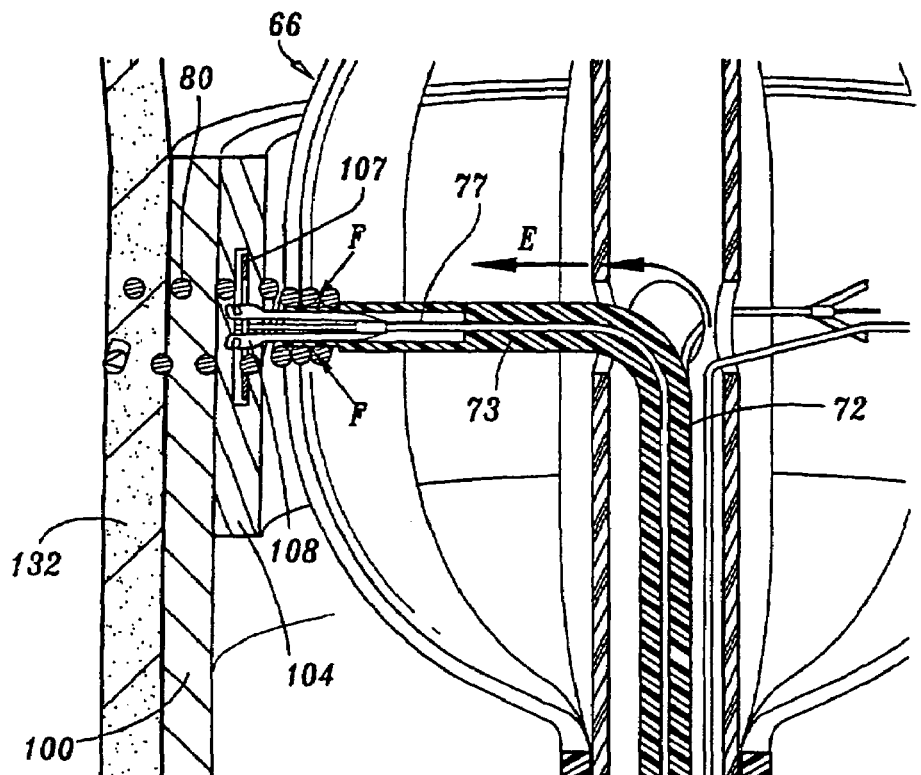
FIG. 26 is a perspective view, in part cross-section, showing the drive after the fastener guide is collapsed and the helical fastener deployed.

As shown in FIG. 25, expandable portion 66 supports aortic graft 100 in contact with aortic wall 132. Applicator head 73 of delivery tube 72 is configured and dimensioned to cooperate with inner diameter 84 to advance a helical fastener 80 over multiple guide wires 77, as shown by arrows E. As helical fastener 80 is deployed, anchor legs 108 are caused to collapse, shown by arrows F in FIG. 26. Delivery tube 72 causes rotational movement of helical fastener 80 and corresponding penetration of band 104, aortic graft 100 and aortic wall 132, facilitating fastening.

Figure 27:
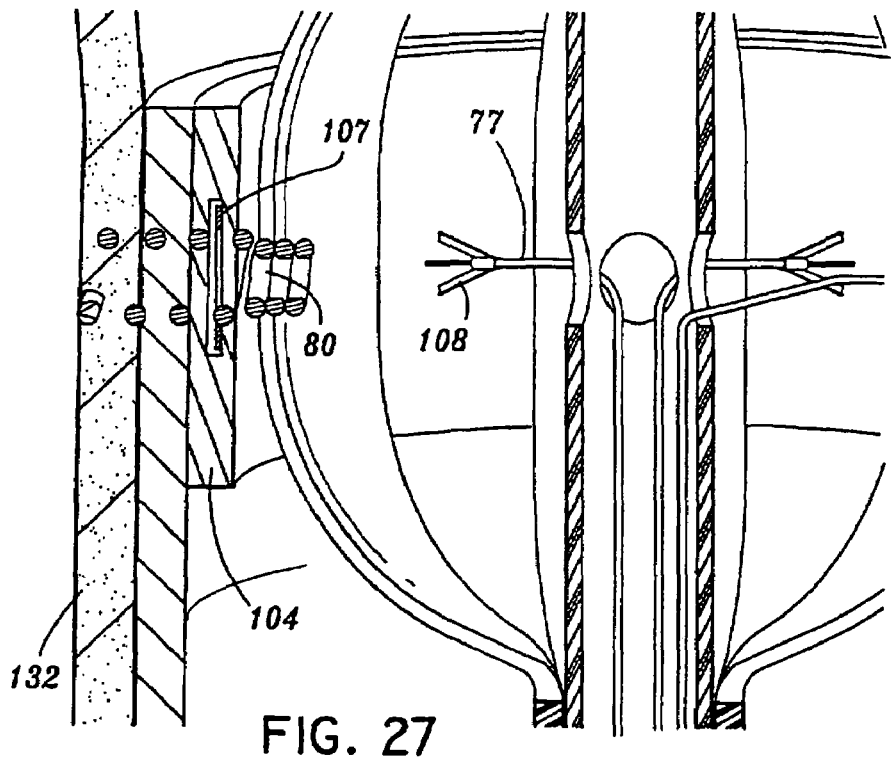
FIG. 27 is a perspective view, showing retraction of the drive and fastener guide.

Delivery tube 72 is retracted subsequent to deployment of helical fastener 80 and multiple guide wire 77 is also retracted, as shown in FIG. 27, with helical fastener 80 in a deployed position. Delivery tube 72 is subsequently loaded with another helical fastener 80 for deployment from another of multiple guide wires 77. As many helical fasteners 80 may be deployed as are necessary to adequately fasten aortic graft 100 to aortic wall 132. It is contemplated that at least a portion of the fastener guides and/or guide wires may remain fixed to the prosthetic upon deployment of a fastener.

Figure 28:
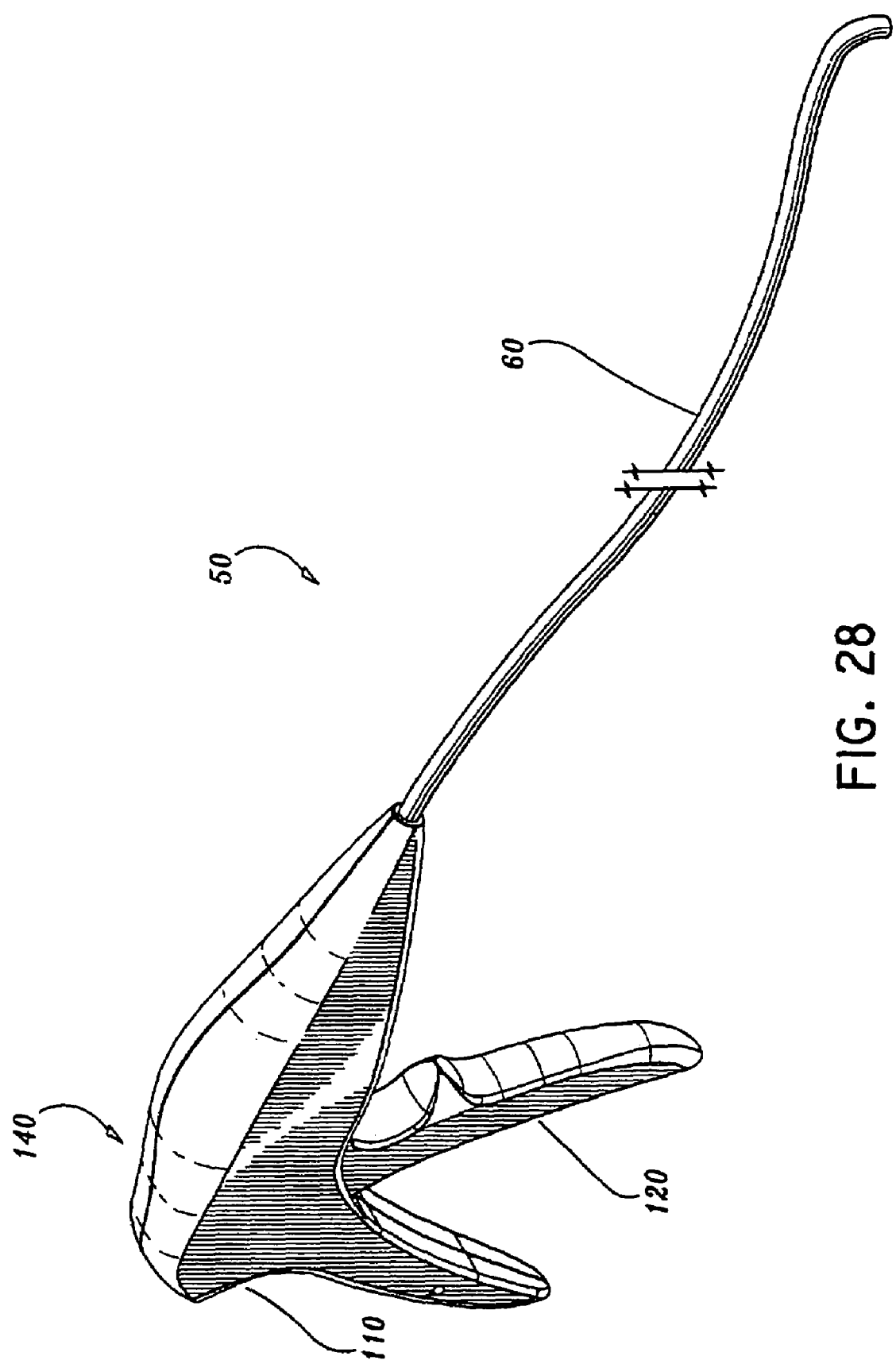
FIG. 28 is a perspective view of an alternate embodiment of the control assembly.

In another embodiment as shown in FIG. 28, control assembly 140 includes a handle 110 and a trigger 120 for controlling operation of endovascular fastener applicator 50. In this embodiment, handle 110 controls advancement of delivery tube 72 (not shown) and trigger 120 controls advancement of drive assembly 76 (not shown) and deployment of helical fasteners 80 (not shown).

Figure 33:
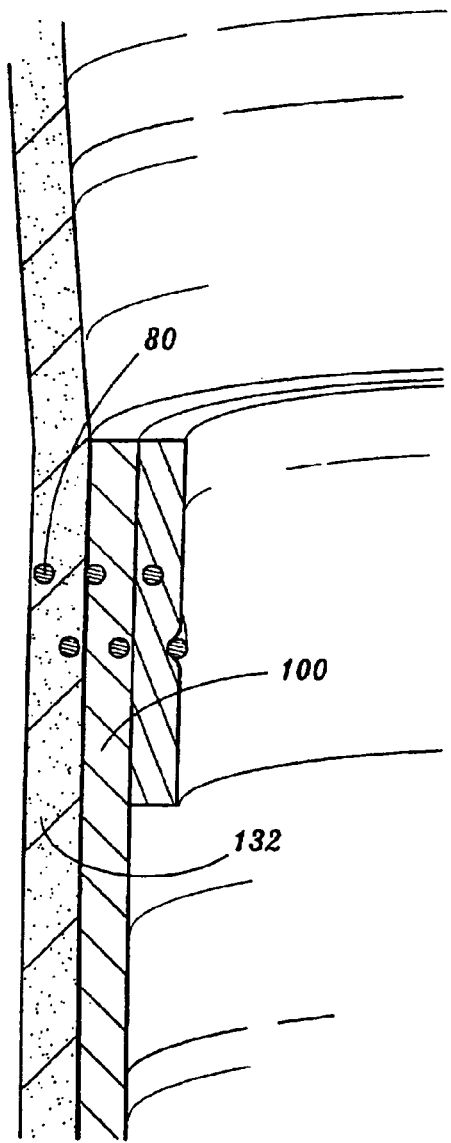
FIG. 33 is a perspective view of the helical fastener deployed into the prosthesis and artery.
Figure 32:
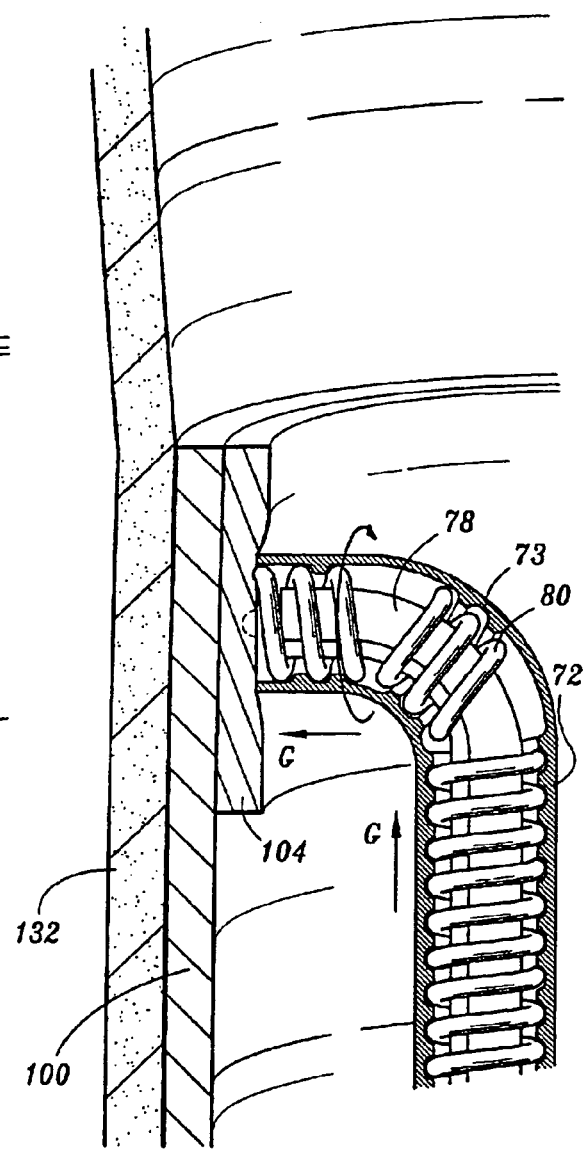
FIG. 32 is a perspective view of an applicator head and helical fasteners prior to deployment into a prosthesis.

In another embodiment, as illustrated in FIGS. 29-33, a plurality of helical fasteners 80 are loaded in endovascular fastener applicator 50 for deployment. As shown in FIG. 30, drive assembly 76 defines a channel 75 for accepting helical fasteners 80(FIG. 31). In particular, penetration limit end 82 of helical fastener 80 slidably engages channel 75 providing a plurality of helical fasteners 80 for deployment, as shown in FIG. 29. Applicator head 73 of delivery tube 72 engages band 104, as shown in FIG. 32, and drive assembly 76 advances helical fasteners 80 to penetrate band 104, aortic graft 100 and aortic wall 132, shown by arrows G. As shown in FIG. 33, aortic graft 100 is fastened to aortic wall 132 of aorta 124 by helical fastener 80. After deployment of a helical fastener 80, delivery tube 72 is rotated to deploy another of the plurality of helical fasteners 80, consequently reloading is not required.

In another embodiment, as illustrated in FIGS. 34-51, expandable portion 66 is capable of moving between two extreme positions. A relaxed position, as shown in FIG. 35, and an expanded position, as shown in FIG. 34. In the embodiment illustrated in FIG. 34, expandable portion 66 includes support members 67 that define open interstitial regions 70.

Figure 36:
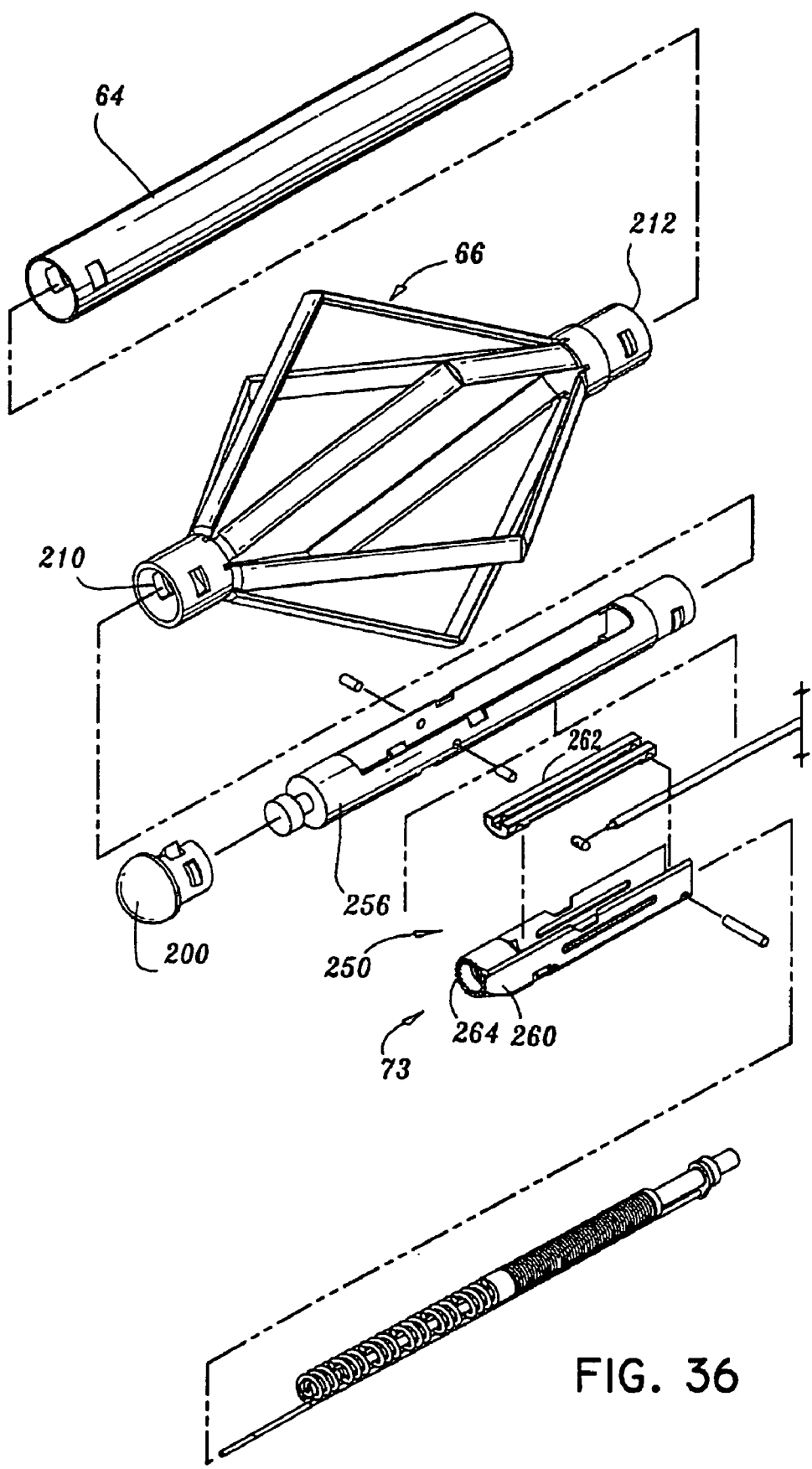
FIG. 36 is an exploded view of the delivery assembly shown in FIG. 34.

As best shown in FIG. 36, outer sleeve 64 operatively engages with expandable portion 66 for controlling operation between the two extreme positions. Expandable portion 66 has an atraumatic head 200 attached to opening 210 defined at the distal end of expandable portion 66 and opening 212 defined at its proximal end for receiving applicator head 73 of delivery tube 72. Applicator head 73 includes ejection mount 250 for deployment of a plurality of helical fasteners 80 from drive assembly 76.

Ejection mount 250, as shown in FIG. 36, includes yoke 256 and ejection head 260. Yoke 256 engages penetration head 200 for coaxial positioning within expandable portion 66. Ejection head 260 is pivotally positioned within yoke 256. Ejection head 260 includes a cam divider 262 and a saw-toothed face 264. Ejection head 260 is capable of rotational movement relative to delivery tube 72 and pivotal movement between two extreme positions. A first extreme position is coaxial with delivery tube 72 and a second extreme position is perpendicular to the longitudinal axis of delivery tube 72 and in position to deploy a helical fastener 80.

With reference to FIGS. 37 and 38, drive assembly 76 includes distal drive 280, proximal drive 284, outer drive 285, ratchet assembly 286, spring 294 and washer 296. Distal drive 280 defines a slot 281 for receiving penetration limit end 82 for loading a plurality of helical fasteners 80. The plurality of helical fasteners 80 are spring loaded onto drive assembly 76 and separated from spring 294 by washer 296.

Distal drive 280 is operatively connected to ratchet assembly 286 which is operatively connected to proximal drive 284 and outer drive 285. Ratchet assembly 286 includes ratchet sleeve 287 which defines opening 288 for receipt of distal drive 280. Manipulation of proximal drive 284 causes movement of distal drive 280 to facilitate deployment of helical fasteners 80. Ratchet sleeve 287 also defines opening 289 for receipt of proximal drive 284. Ratchet sleeve 287 is slidably received within ratchet retainer 290 for cooperative engagement with outer drive 285. Ratchet retainer 290 defines opening 291 for receiving ratchet arm 292.

As shown in FIGS. 39 and 40, ratchet arm 292 engages ejection head 260. Ratchet arm 292 is positioned within cam divider 262 in ejection head 260 and secured therein by set screw 298. It is contemplated that ratchet arm 292 is crimped in place within ejection head 260 and that no set screw is required. It is further contemplated that ratchet arm 292 may be fixed within ejection head 260 as is known by one skilled in the art. Manipulation of outer drive 285 engages ratchet retainer 290 and ratchet arm 292 causing pivotal movement of ejection head 260 relative to delivery tube 72.

Figures 41, 42:
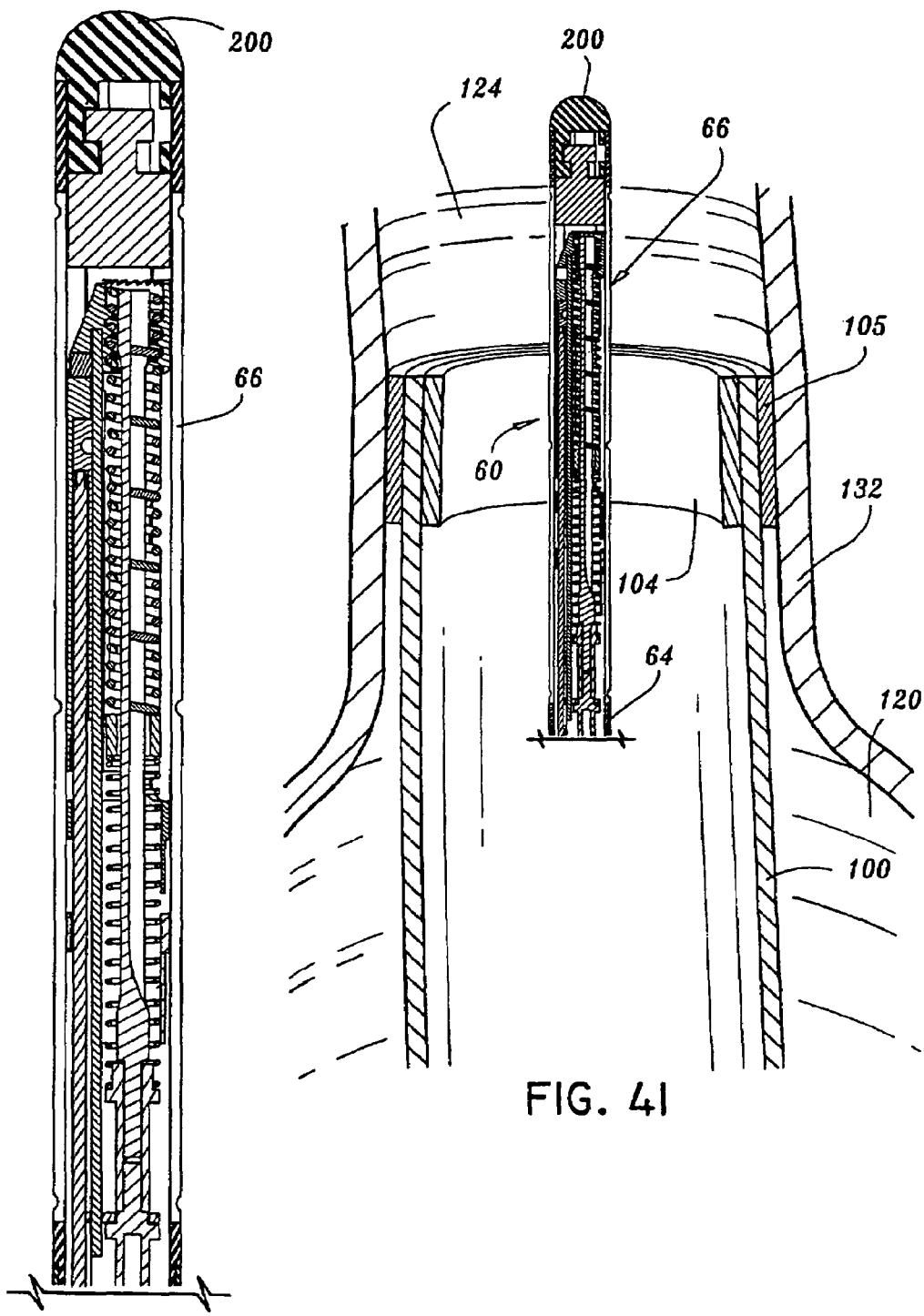
FIG. 41 is a cross-sectional view of the applicator with the expandable portion in a relaxed state and a prosthetic having a sealing gasket.
FIG. 42 is a cross-sectional view, in part elevation, of the distal end of the applicator.

As illustrated in FIGS. 41 and 42, delivery assembly 60 is positioned at the aneurysm site of abdominal aortic aneurysm 120. Aortic graft 100 is positioned for fastening to aortic wall 132 of aorta 124. Aortic graft 100 has band 104. Aortic graft 100 may also have gasket 105, as shown in FIG. 41, sewn to the outside diameter of aortic graft 100 to prevent leakage of fluid.

Figures 43, 44:
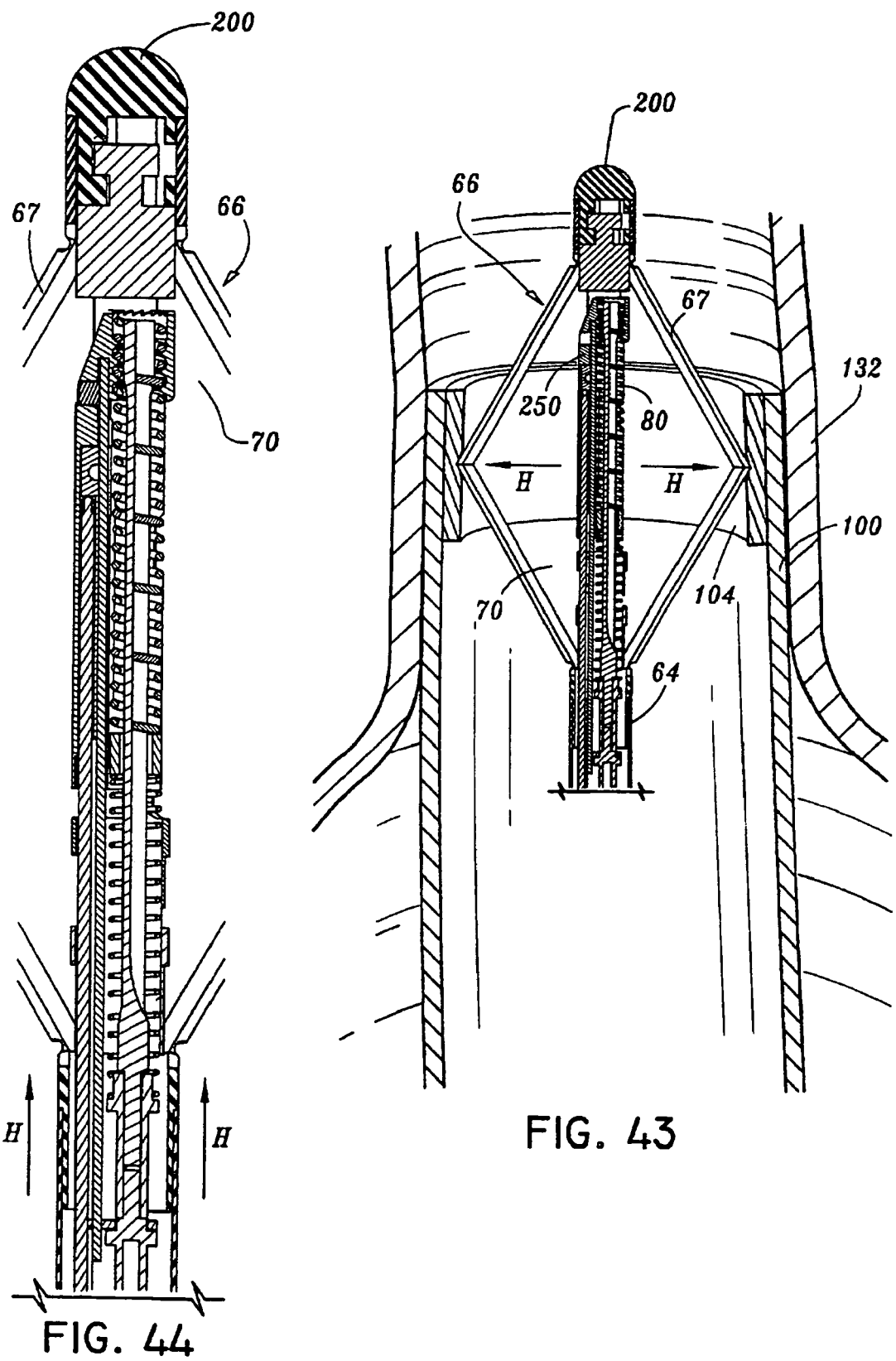
FIG. 43 is a cross-sectional view, in part elevation, with the expandable portion in an expanded state.
FIG. 44 is an enlarged cross-sectional view, in part elevation, of the distal end of the applicator.

Expandable portion 66 is in a relaxed state, as shown in FIGS. 41 and 42. Aortic graft 100 is positioned at the abdominal aneurysm site and expandable portion 66 is caused to expand by axial motion of outer sleeve 64, shown by arrows I in FIG. 44 and by arrows H in FIG. 43, illustrating the outward force of support members 67 used to support aortic graft 100 in contact with aortic wall 132. Expandable portion 66 facilitates fastening of aortic graft 100 with aortic wall 132 for deployment of helical fasteners 80 by securing aortic graft 100 in contact with aortic wall 132. It is contemplated that helical fasteners 80 may be deployed from ejection mount 250 through interstitial regions 70 between support members 67. The helical fasteners 80 are deployed about the circumference of aortic graft 100 relative to the number of support members 67 and spacing of interstitial regions 70.

Figure 45:
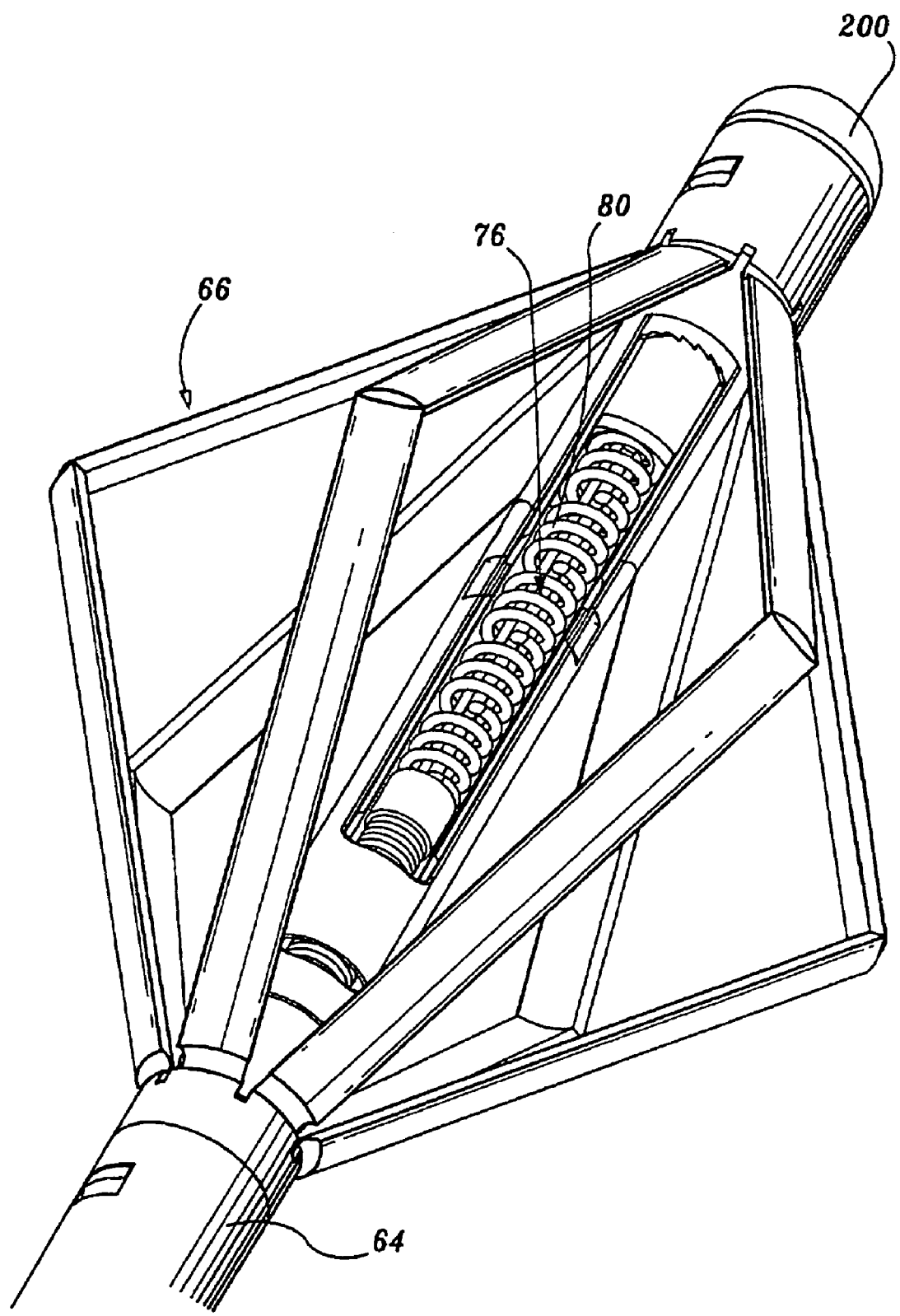
FIG. 45 is a perspective view of the expandable portion in an expanded state and the ejection mount loaded with helical fasteners.
Figure 46:
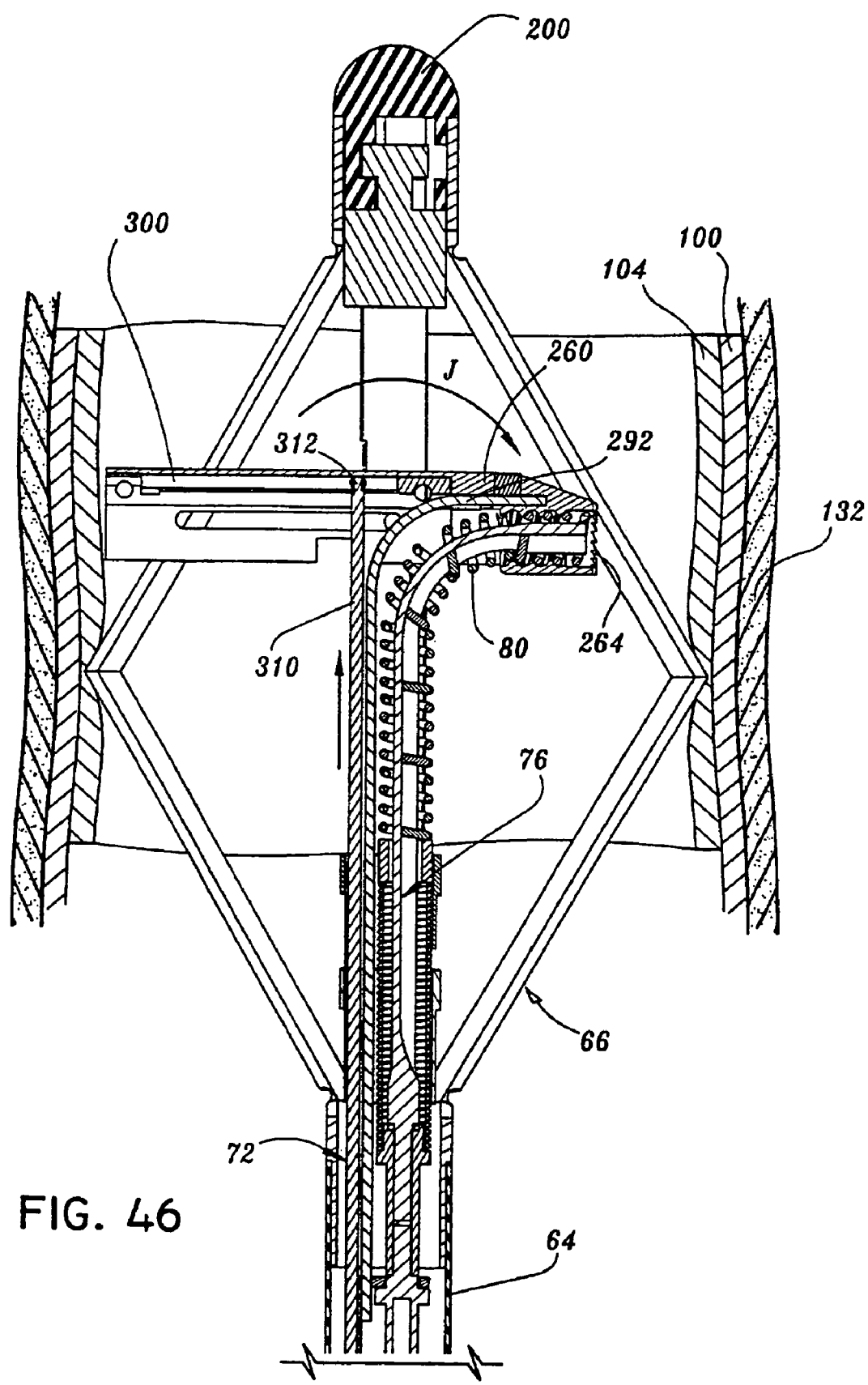
FIG. 46 is a cross-sectional view, in part elevation, with the ejection mount pivoted for deployment of helical fasteners.

As shown in FIG. 45, drive assembly 76 is loaded with a plurality of helical fasteners 80. Referring to FIG. 46, delivery tube 72 has an ejection arm 310 positioned at its distal end facilitating pivotal movement of ejection mount 250. An arm 292 functions as an ejection arm to ejection head 260. This provides extra holding force on the graft which pivots ejection head 260 positioned at its distal end. Ejection arm 310 includes a slider 312 received within a cam slot 300 defined by ejection head 260. Cam slot 300 further defines the relative movable limits of slider 312 and thus ejection arm 310.

Delivery tube 72 is manipulated advancing ejection arm 310 axially causing pivotal movement of ejection head 260, shown by avow J, and positioning ejection head 260 for deployment of helical fasteners 80. Ejection head 260 is positioned in a substantially perpendicular orientation to the longitudinal axis of delivery tube 72.

Figure 46A:
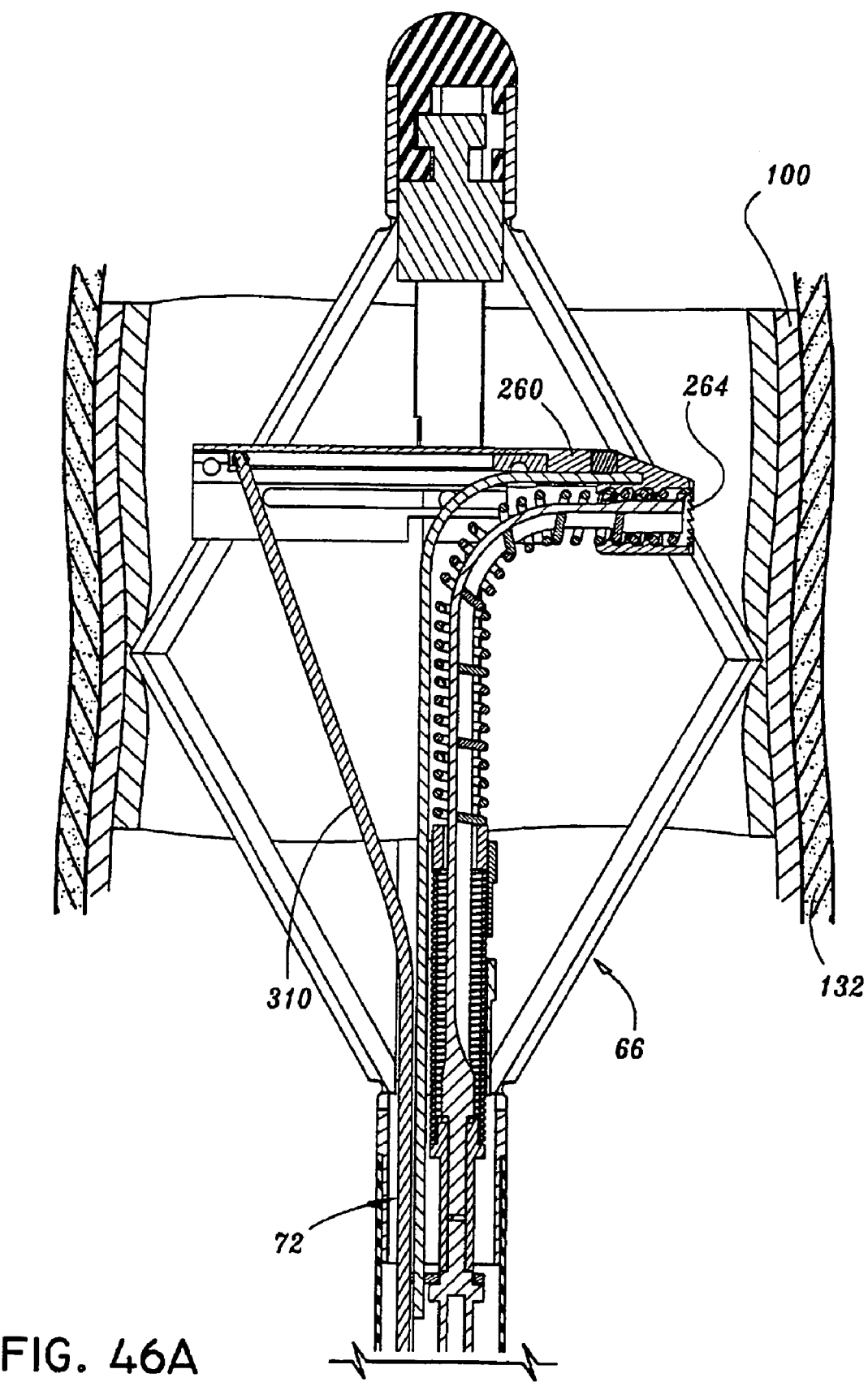
FIG. 46A is a perspective view, in part cross-section, an alternate embodiment of the ejection mount pivoted for deployment of helical fasteners.

It is contemplated that ejection arm 310 has alternate orientations for causing movement of ejection head 260. For example, in an alternate embodiment shown in FIG. 46A, ejection head 260 pivots within expandable portion 66 and is positioned at the center of expandable portion 66. Saw-toothed face 264 is positioned at a closer proximity to the inner surface of graft 100 for accurate deployment of a fastener. At the center position, ejection head 260 spans a diameter that expandable portion 66 supports aortic graft 100 in contact with aortic wall 132. In this embodiment, ejection arm 310 is fixed at a maximum angle relative to delivery tube 72.

Figure 47:
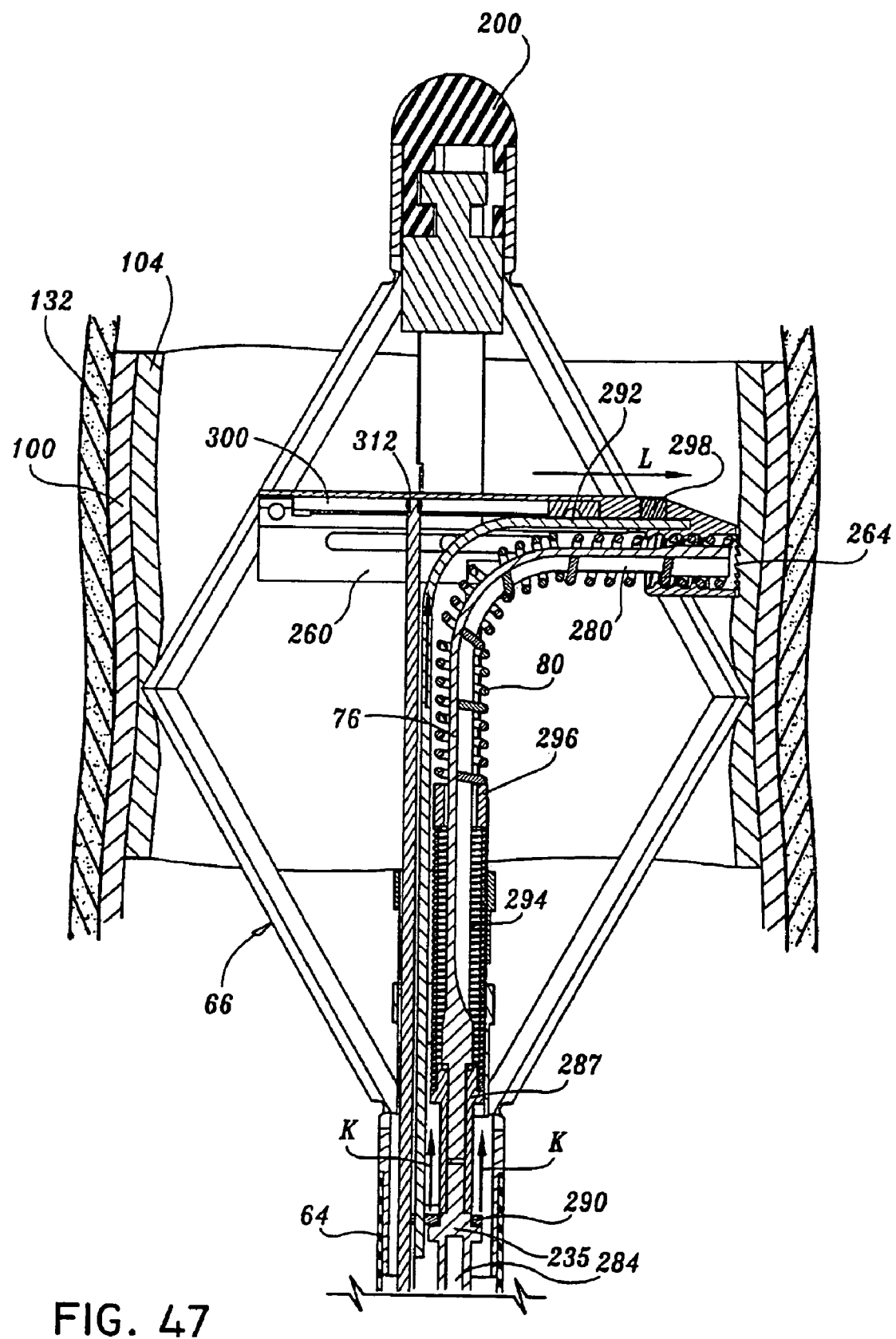
FIG. 47 is a cross-sectional view, in part elevation, of the ejection mount engaging the aortic graft prior to deployment of helical fasteners.

Drive assembly 76 is manipulated so that ejection head 260 engages band 104 of aortic graft 100 for deployment of helical fasteners 80, as illustrated in FIG. 47. Outer drive 285 and proximal drive 284 are advanced, shown by arrows K. Ejection arm 292 correspondingly axially positions saw-tooth face 264 of ejection head 260 to contact band 104 of aortic graft 100, as shown by arrow L. Ejection arm 292 may also cause rotational movement of ejection head 260 and saw-tooth face 264 for engaging aortic graft 100.

With reference to FIG. 48, distal drive 280 advances and is rotated causing helical fasteners 80 to penetrate and fasten aortic graft 100 and aortic wall 132, as shown by arrow M.

As shown in FIG. 49, delivery tube 72 is manipulated so that ejection arm 310 pivotally retracts ejection head 260 to a position substantially parallel to the longitudinal axis of delivery tube 72, as shown by arrows MM.

Figure 50:
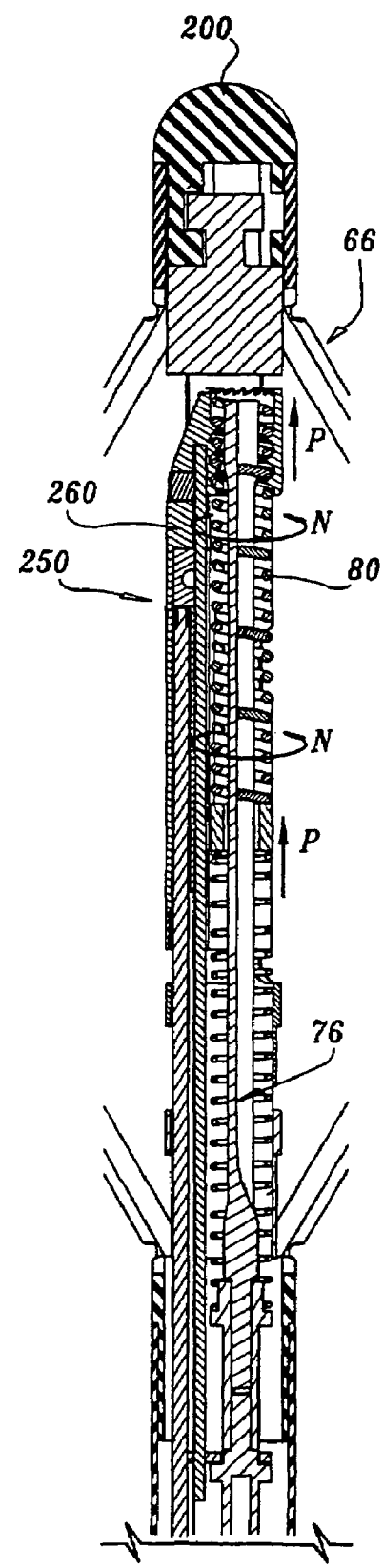
FIG. 50 is a cross-sectional view, in part elevation, showing the ejection mount subsequent to deployment of a helical fastener.

FIG. 50 illustrates a retracted ejection mount 250 subsequent to deployment of one of a plurality of helical fasteners 80. A rotational force is transmitted from the proximal end to the distal end of drive assembly 76, shown by arrows N, thereby driving and axially advancing another of the plurality of helical fasteners 80, shown by arrows P, for deployment by ejection head 260 at a new deployment site.

Figure 51:
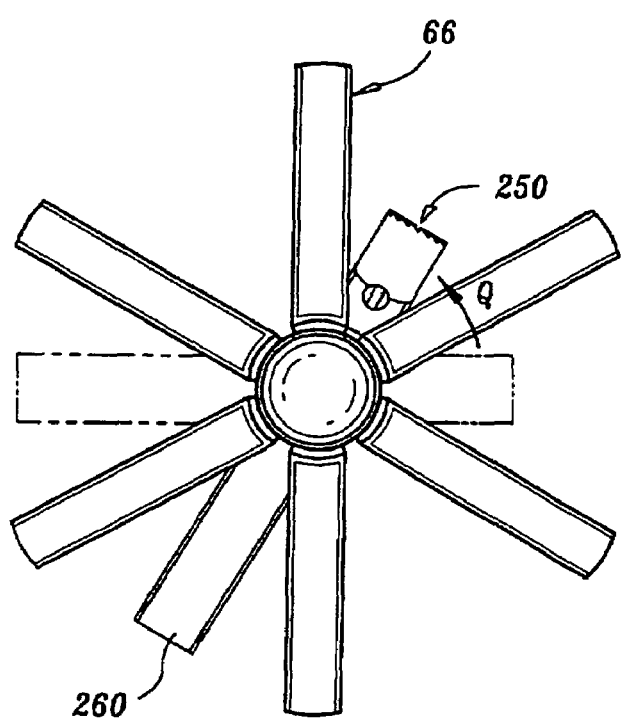
FIG. 51 is a top view of the applicator, showing movement of the ejection mount prior to deployment of a helical fastener.

FIG. 51 shows ejection head 260 positioned in a substantially perpendicular orientation to the longitudinal axis of delivery tube 72 (not shown). Ejection head 260 is rotated to a new deployment site to deploy another of the plurality of helical fasteners 80 (not shown). As many helical fasteners 80 may be deployed as are necessary to adequately fasten aortic graft 100 to aortic wall 132.

It will be understood that various modifications may be made to the embodiments disclosed herein. For example, while specific preferred embodiments of the endovascular fastener applicator have been described in detail, structures that perform substantially the same function in substantially the same way to achieve substantially the same result may also be used. For example, the expandable portion may include expanding wires for supporting a prostheses in contact with a vessel wall. Also the fastener guide may be implanted completely through the thickness of the aortic graft. Further, the helical fasteners may be constructed from various suitable materials or may embody one continuous fastener that is severable at the point of insertion. Therefore, the above description should not be construed as limiting, but merely as exemplifications of preferred embodiments, those skilled in the art will envision other modifications within the scope and spirit of the present disclosure.

Features and advantages of the invention are set forth in the following claims.

I claim:
1. A method comprising
   advancing a graft for repairing an aneurysm in a blood vessel lumen,
   advancing within the blood vessel lumen an elongated endovascular device, the elongated endovascular device including a spiral suture applicator including a rotary head, a tissue-piercing spiral suture carried by the rotary head for advancement into a vascular wall of the blood vessel lumen in response to operation of the rotary head, and a component that is sized and configured to be moved between a contracted position and an operating condition that makes selective engagement against a vascular wall within the blood vessel, the endovascular device being advanced within the blood vessel lumen while the component is in the contracted position,
   applying a stabilization force within the blood vessel by moving the component into the operating condition to make selective engagement against a vascular wall of the blood vessel, and
   securing the graft to a vascular wall of the blood vessel to repair the aneurysm by operating the rotary head from a region remote from the blood vessel lumen to advance the tissue-piercing spiral suture into the vascular wall while the stabilization force is applied within the blood vessel lumen by the component.

2. A method according to claim 1
   wherein the component is moved between a contracted position and an operating condition by expansion.

* * * * *